United States Patent
Ko et al.

(10) Patent No.: US 9,469,586 B2
(45) Date of Patent: Oct. 18, 2016

(54) PRODUCTION OF PARTIALLY REFINED WASTE GLYCEROL

(71) Applicant: REG Life Sciences, LLC, Ames, IA (US)

(72) Inventors: Myong K. Ko, San Mateo, CA (US);
Perry Y. Liao, Daly City, CA (US);
Simon Li, San Francisco, CA (US);
Fernando A. Sanchez-Riera, San Carlos, CA (US)

(73) Assignee: REG LIFE SCIENCES, LLC, Ames, IA (US)

( * ) Notice: Subject to any disclaimer, the term of this patent is extended or adjusted under 35 U.S.C. 154(b) by 118 days.

(21) Appl. No.: 14/463,635

(22) Filed: Aug. 19, 2014

(65) Prior Publication Data

US 2016/0052847 A1 Feb. 25, 2016

Related U.S. Application Data

(60) Provisional application No. 61/867,473, filed on Aug. 19, 2013.

(51) Int. Cl.
*C07C 29/86* (2006.01)
*C11D 19/00* (2006.01)

(52) U.S. Cl.
CPC .............. *C07C 29/86* (2013.01); *C11D 19/00* (2013.01)

(58) Field of Classification Search
CPC ...................................................... C11D 19/00
USPC ......................................................... 568/869
See application file for complete search history.

(56) References Cited

U.S. PATENT DOCUMENTS

| | | |
|---|---|---|
| 4,164,507 A | 8/1979 | Blytas et al. |
| 4,560,812 A | 12/1985 | Blytas |
| 7,667,081 B2 | 2/2010 | Rezkallah |
| 7,718,833 B2 | 5/2010 | Potthast et al. |
| 8,097,439 B2 | 1/2012 | Alibhai et al. |
| 8,110,093 B2 | 2/2012 | Friedman et al. |
| 8,110,670 B2 | 2/2012 | Hu et al. |
| 8,183,028 B2 | 5/2012 | Alibhai et al. |
| 8,268,599 B2 | 9/2012 | Schirmer et al. |
| 8,283,143 B2 | 10/2012 | Hu et al. |
| 8,313,934 B2 | 11/2012 | Bhatia et al. |
| 8,314,205 B2 | 11/2012 | Gilbeau et al. |
| 8,323,924 B2 | 12/2012 | Schirmer et al. |
| 8,372,610 B2 | 2/2013 | Lee et al. |
| 2009/0137851 A1 | 5/2009 | Potthast et al. |

FOREIGN PATENT DOCUMENTS

EP    2 159 212    3/2010

OTHER PUBLICATIONS

Yang, et al., Value-added uses for crude glycerol-a byproduct of biodiesel production, Biotechnology for Biofuels, (2012), 5:13.

(Continued)

*Primary Examiner* — Elvis O Price
(74) *Attorney, Agent, or Firm* — Foley & Lardner LLP

(57) ABSTRACT

The disclosure relates to a novel glycerol purification process that produces partially refined waste glycerol for a variety of industrial applications. The disclosure encompasses a salt-containing partially refined glycerol composition that is suitable as a fermentation grade glycerol.

28 Claims, 7 Drawing Sheets

(56) References Cited

OTHER PUBLICATIONS

Anneken, David J., "Glycerine a Key Cosmetic Ingredient", Cosmetic Science and Technology Series (1991), Chapter 3: Manufacture of Glycerine from Natural Fats and Oils.

Gervajio, Gregorio C., "Fatty Acids and Derivatives from Coconut Oil", Bailey's Industrial Oil and Fat Products, Sixth Edition, Six Volume Set (2005), pp. 1-37.

Schroeder, Keith, "Glycerine", Bailey's Industrial Oil and Fat Products, Sixth Edition, Six Volume Set (2005), Chapter 5, pp. 191-222.

Cimbria Sket CIMM X (KL) (2008), "Glycerine Distillation (Refining) Technology", Slides 1-14.

SRS Engineering Corporation, "What is Glycerin?", http://c1-preview.prosites.com/37030/wy/docs/Glycerin%20Purification.pdf.

International Search Report for International Application No. PCT/US2014051757 mailed Nov. 28, 2014.

PRODUCTION OF PARTIALLY REFINED WASTE GLYCEROL

FIELD

The disclosure relates to a novel glycerol purification process that produces partially refined waste glycerol for a variety of industrial applications. Herein, the disclosure encompasses a salt-containing partially refined glycerol composition that is suitable as a fermentation grade glycerol.

BACKGROUND

Biodiesel is a natural and renewable domestic fuel alternative for diesel engines made from vegetable oils and fats. Because it is nontoxic and biodegradable it has become a promising alternative to fuels made from petroleum. Biodiesel burns clean. Thus, it results in a significant reduction of the types of pollutants that contribute to smog and global warming. Biodiesel emits up to 85 percent fewer cancer-causing agents and is the only alternate fuel approved by the Environmental Protection Agency (EPA). It has passed every Heath-Effects Test of the Clean Air Act and meets the requirements of the California Air Resources Board (CARB). Although, biodiesel is still relatively costly to make, the utilization of its co-product glycerol is one of the promising options for off-setting the biodiesel production cost.

Glycerol has more than 1500 known applications in many different industries ranging from foods, pharmaceuticals, and cosmetics (i.e., USP grade glycerol) to paints, coatings and other industrial types of uses (i.e., technical grade glycerol). It is the most versatile and valuable by-product created during biodiesel production. One gallon of biodiesel generates about 1.05 pounds of crude glycerol. A 30-million-gallon-per-year plant generates about 11,500 tons of 99.9 percent pure glycerol. It is speculated that the world market will generate approx. 37 billion gallons of biodiesel by 2016, suggesting a production of 4 billion gallons or 16.5 million metric tons of crude glycerol. This is believed to create too much of a crude glycerol surplus which may negatively impact the refined glycerol market (Yang et al. (2012) *Biotechnology for Biofuels* 5:13). According to the EPA, this impure form of glycerol must be disposed of within a certain period of time, leading to high disposal fees for companies that produce glycerol as a by-product. Hence, the development of sustainable methods for utilizing raw organic glycerol is desirable while it is equally desirable not to offset the balance of crude to refined product.

Most biodiesel productions use homogeneous alkaline catalysts such as sodium methylate. The transesterification of triacylglycerides with methanol creates a methyl-ester phase and a glycerol phase. Impurities, including catalyst, soap, methanol and water are usually concentrated in the glycerol phase. The glycerol phase is generally neutralized with acid and the cationic component of the catalyst is incorporated as a salt. Thus, it is not uncommon that glycerol, as a by-product of the biodiesel production, has a salt content of 5 to 7 percent. This high salt content makes conventional purification techniques cost intensive. There are various methods for purifying crude glycerol, including fractional distillation, membrane technology employing a series of NF and RO membrane stages (NF/RO membrane), electro-dialysis membrane technology (electro-dialysis membrane), bipolar membrane technology (bi-polar membrane), and ion-exchange resin adsorption technology (ion-exchange resin adsorption). Fractional distillation is the most commonly practiced method. It results in high purity glycerol at high yields, however, it is also capital-, labor-, and energy-intensive. Glycerol has a high heat capacity and, thus, requires a high-energy input for vaporization. Another common technique for glycerol purification is the classical ion-exchange method. But the higher salt content of glycerol as a result of biodiesel production makes classical ion-exchange an uneconomical choice. Particularly, the chemical regeneration cost for the resins becomes too high when the salt content in glycerol approaches 5 to 7 percent.

Most methods that are used to purify glycerol are based on aqueous technologies that use crude glycerol water, i.e., they use glycerol that contains about 60 to 70 percent water as a feed. Fractional distillation refines glycerol by using crude glycerol that contains about 6 to 8 percent water that has gone through methanol rectification and water evaporation. Amongst all the available technologies, the electro-dialysis membrane, bi-polar membrane and ion-exchange resin adsorption are mainly desalting processes. They all require separate deoiling (i.e., deoiling) process steps and generate large amounts of waste water. The ion-exchange resin adsorption method is mainly used for low salt polishing applications. The NF/RO membrane uses a multi-stage membrane unit for the glycerol refining process that is capable of both desalting and deoiling the glycerol.

There are also hybrid systems for purifying crude glycerol. For example, a hybrid system for purifying glycerol can employ a membrane technology as a main process and distillation as a minor process, wherein both can recover glycerol in so-called concentrate and permeate streams. In that type of system, the concentrate stream contains dirty glycerol water while a permeate stream contains cleaner glycerol water. The glycerol contained within the concentrate streams can be recovered or discharged as a loss. Each stage that contains a permeate stream in a process that applies any of the membrane technologies (i.e., a membrane process) contains glycerol-water intermediates with reduced salt and reduced organics. Each stage that contains a concentrate stream in a membrane process contains glycerol, water, concentrated salt and concentrated organic impurities. Fractional distillation can also be used in a hybrid system. Fractional distillation is similar to a membrane system in that it is capable of desalting and deoiling the glycerol but it relies on continuous salt removal under high vacuum. A hybrid system employing fractional distillation recovers glycerol in the concentrate stream of the membrane process.

Although, both fractional distillation and NF/RO membrane produce glycerol suitable for fermentation, the high production cost creates a down side. Currently, the majority of large industrial commercial processes employ fractional distillation. The equipment cost of fractional distillation of crude glycerol is high due to the need of continuous salt removal under high vacuum (see, e.g., Glycerine a Key Cosmetic Ingredient, Cosmetic Science and Technology Series (1991) by Marcel Dekker, Inc; and Bailey's Industrial Oil and Fat Products, Sixth Edition, Six Volume Set (2005) by John Wiley and Sons, Inc.).

Purified or refined glycerol (i.e., USP grade glycerol) has numerous applications from fragrances to cosmetics to pharmaceuticals and is a valued commercial product. The production of purified glycerol is costly because the majority of existing methods of purification employ fractional distillation (supra). However, USP grade glycerol is not suitable for all applications because it is simply too costly to manufacture and unnecessarily pure for industrial applications (e.g., paints, coats, adhesives, etc.). Technical grade glycerol is more suitable for industrial applications but its production also relies on fractional distillation and it is therefore not a cost-effective alternative. Thus, a method is needed that produces a form of technical grade glycerol at a low enough cost that is acceptable for industrial applications. In addition, there is a need for a new form of technical grade glycerol with characteristics that meet the specifications required for renewable methods and bio-degradable products that reach beyond those that rely mostly on refined or crude glycerol. The present disclosure addresses this need.

SUMMARY

One aspect of the disclosure provides a process of producing partially refined waste glycerol by refining crude glycerol containing organic impurities, wherein the process includes deoiling using a hydrophobic solvent to extract the organic impurities; dewatering by drying at an elevated temperature; and desalting using a polar solvent to precipitate salt.

Another aspect of the disclosure provides a process of producing partially refined waste glycerol by refining crude glycerol containing organic impurities, wherein the process includes subjecting the crude glycerol to a hydrophobic solvent to produce a mixture of crude glycerol and hydrophobic solvent; and separating the mixture of crude glycerol and hydrophobic solvent to produce a deoiled (DO) glycerol and a phase containing hydrophobic solvent and organic impurities. In one aspect, the process further includes the step of drying the DO glycerol to produce a deoiled and dewatered (DOW) glycerol. In another aspect, the process further includes the steps of subjecting a polar solvent to the DOW glycerol to produce a mixture of polar solvent and DOW glycerol and precipitating salt from the mixture of polar solvent and DOW glycerol; and separating the mixture of polar solvent and DOW glycerol into a light phase containing a deoiled, dewatered and desalted (DOWS) glycerol and the polar solvent and a heavy phase containing the salt. In another aspect, the process further includes the step of removing the polar solvent from the light phase to produce a purified DOWS glycerol. In another aspect, the process further includes the step of partially evaporating the DOW glycerol before subjecting it to the polar solvent. In one embodiment, the DOWS glycerol is fermentation grade glycerol. In another embodiment, the fermentation grade glycerol is salt-containing glycerol. In another embodiment, the hydrophobic solvent is selected from triacylglyceride, alkane, alkene, acetate, and/or fatty acid alcohol ester. In still another embodiment, the triacylglyceride is vegetable oil. In still another embodiment, the acetate is butyl acetate. In yet another embodiment the alkane is hexane. In another embodiment the process includes organic impurities that are oil-soluble. In one embodiment, the DO glycerol includes less than about 195 ppm oil-soluble organic impurities. In another embodiment, the DOW glycerol includes less than about 0.5 percent water. In another embodiment, the polar solvent is alcohol. In one embodiment, the alcohol is isopropanol or butanol. In another embodiment, the step of removing the polar solvent is done by flash evaporation.

Another aspect of the disclosure provides a process of producing partially refined waste glycerol by refining crude glycerol containing organic impurities, wherein the process includes subjecting the crude glycerol to a hydrophobic solvent to produce a mixture of crude glycerol and hydrophobic solvent; and separating the mixture of crude glycerol and hydrophobic solvent to produce a deoiled (DO) glycerol and a phase containing hydrophobic solvent and organic impurities. In one aspect, the process further includes the steps of subjecting a polar solvent to the DO glycerol to produce a mixture of polar solvent and DO glycerol and precipitating salt from the mixture of polar solvent and DO glycerol; and separating the mixture of polar solvent and DO glycerol into a light phase containing a deoiled and desalted glycerol and the polar solvent and a heavy phase containing the salt. In another aspect, the process further includes the step of drying said deoiled and desalted glycerol to produce a deoiled, desalted and dewatered (DOWS) glycerol. In one embodiment, the DOWS glycerol is fermentation grade glycerol. In another embodiment, the fermentation grade glycerol is salt-containing glycerol. In another embodiment, the hydrophobic solvent is selected from triacylglyceride, alkane, alkene, acetate, and/or fatty acid alcohol ester. In still another embodiment, the triacylglyceride is vegetable oil. In still another embodiment, the acetate is butyl acetate. In yet another embodiment the alkane is hexane. In another embodiment the process includes organic impurities that are oil-soluble. In one embodiment, the DO glycerol includes less than about 195 ppm oil-soluble organic impurities. In another embodiment, the DOW glycerol includes less than about 0.5 percent water. In another embodiment, the polar solvent is alcohol. In one embodiment, the alcohol is isopropanol or butanol. In another embodiment, the step of removing the polar solvent is done by flash evaporation.

The disclosure further contemplates a process as described above (supra) that further includes the step of tailoring the salt content of a fermentation grade glycerol. In one embodiment, the process includes tailoring the salt content of a fermentation grade glycerol to between about 0.05 to about 8.2 percent salt. In another embodiment, the process includes tailoring the salt content of a fermentation grade glycerol to between about 0.05 to about 3.5 percent salt. In another embodiment, the process includes tailoring the salt content of a fermentation grade glycerol to between about 0.05 to about 1.0 percent salt.

Another aspect of the disclosure provides a process of producing partially refined waste glycerol by refining crude glycerol containing organic impurities, wherein the process includes subjecting the crude glycerol to a hydrophobic solvent to produce a mixture of crude glycerol and hydrophobic solvent; and separating the mixture of crude glycerol and hydrophobic solvent to produce a deoiled (DO) glycerol and a phase containing hydrophobic solvent and organic impurities. In one embodiment, the separation occurs by at least one of gravity decantation, hydrocyclone separation, and/or centrifugal separation. In one aspect, the process further includes the step of heating the mixture of crude glycerol and hydrophobic solvent. In one embodiment, the process includes the step of heating the mixture of crude glycerol and hydrophobic solvent to between about 20° C. to about 95° C. In another embodiment, the process includes the step of heating the mixture of crude glycerol and hydrophobic solvent to between about 55° C. to about 65° C. In another aspect, the process further includes the step of mixing the mixture of crude glycerol and hydrophobic solvent. In one embodiment, the process includes the step of mixing the mixture of crude glycerol and hydrophobic solvent for between about 5 minutes to about 30 minutes.

Another aspect of the disclosure provides a process of producing partially refined waste glycerol by refining crude glycerol containing organic impurities, wherein the process includes subjecting the crude glycerol to a hydrophobic solvent to produce a mixture of crude glycerol and hydrophobic solvent; and separating the mixture of crude glycerol and hydrophobic solvent to produce a deoiled (DO) glycerol and a phase containing hydrophobic solvent and organic impurities. In one aspect, the process further includes the step of drying the DO glycerol to produce a deoiled and dewatered (DOW) glycerol. In one embodiment, the drying occurs at between about 60° C. to about 130° C.

The disclosure further contemplates a product produced by the above described processes (supra). In one aspect, the disclosure provides a product produced by a process of producing partially refined waste glycerol by refining crude glycerol containing organic impurities, wherein the process includes deoiling using a hydrophobic solvent to extract the organic impurities; dewatering by drying at an elevated temperature; and desalting using a polar solvent to precipitate salt. In another aspect, the disclosure provides a product produced by a process of producing partially refined waste glycerol by refining crude glycerol containing organic impurities, wherein the process includes subjecting the crude glycerol to a hydrophobic solvent to produce a mixture of crude glycerol and hydrophobic solvent; and separating the mixture of crude glycerol and hydrophobic solvent to produce a deoiled (DO) glycerol and a phase containing hydrophobic solvent and organic impurities. In another aspect, the disclosure provides a product produced by a process of producing partially refined waste glycerol by refining crude glycerol containing organic impurities, wherein the process includes subjecting the crude glycerol to a hydrophobic solvent to produce a mixture of crude glycerol and hydrophobic solvent; separating the mixture of crude glycerol and hydrophobic solvent to produce a deoiled (DO) glycerol and a phase containing hydrophobic solvent and organic impurities; and drying the DO glycerol to produce a deoiled and dewatered (DOW) glycerol. In another aspect, the disclosure provides a product produced by a process of producing partially refined waste glycerol by refining crude glycerol containing organic impurities, wherein the process includes subjecting the crude glycerol to a hydrophobic solvent to produce a mixture of crude glycerol and hydrophobic solvent; separating the mixture of crude glycerol and hydrophobic solvent to produce a deoiled (DO) glycerol and a phase containing hydrophobic solvent and organic impurities; drying the DO glycerol to produce a deoiled and dewatered (DOW) glycerol; subjecting a polar solvent to the DOW glycerol to produce a mixture of polar solvent and DOW glycerol and precipitating salt from the mixture of polar solvent and DOW glycerol; and separating the mixture of polar solvent and DOW glycerol into a light phase containing a deoiled, dewatered and desalted (DOWS) glycerol and the polar solvent and a heavy phase containing the salt. In another aspect, the disclosure provides a product produced by a process of producing partially refined waste glycerol by refining crude glycerol containing organic impurities, wherein the process includes subjecting the crude glycerol to a hydrophobic solvent to produce a mixture of crude glycerol and hydrophobic solvent; separating the mixture of crude glycerol and hydrophobic solvent to produce a deoiled (DO) glycerol and a phase containing hydrophobic solvent and organic impurities; drying the DO glycerol to produce a deoiled and dewatered (DOW) glycerol; subjecting a polar solvent to the DOW glycerol to produce a mixture of polar solvent and DOW glycerol and precipitating salt from the mixture of polar solvent and DOW glycerol; separating the mixture of polar solvent and DOW glycerol into a light phase containing a deoiled, dewatered and desalted (DOWS) glycerol and the polar solvent and a heavy phase containing the salt; and removing the polar solvent from the light phase to produce a purified DOWS glycerol.

The disclosure further encompasses as partially refined waste glycerol derived from the processing of natural fats and oils, wherein the partially refined waste glycerol has reduced salt and/or organic impurities as compared to a crude glycerol. In one embodiment, the partially refined waste glycerol includes a sodium chloride content from between about 0.05 percent to about 8.2 percent. In another embodiment, the partially refined waste glycerol includes a sodium chloride content from between about 0.05 percent to about 3.5 percent. In another embodiment, the partially refined waste glycerol includes a sodium chloride content from between about 0.05 percent to about 2.0 percent. In still another embodiment, the partially refined waste glycerol includes a sodium chloride content from between about 0.05 percent to about 1.0 percent. In another embodiment, the partially refined waste glycerol is a fermentation grade glycerol.

Another aspect of the disclosure provides a process of producing partially refined waste glycerol by refining crude glycerol containing organic impurities, wherein the process includes drying the crude glycerol to produce a dewatered glycerol; subjecting the dewarered glycerol to a hydrophobic solvent to produce a mixture of dewatered glycerol and hydrophobic solvent; and separating the mixture of dewatered glycerol and hydrophobic solvent to produce a deoiled dewatered (DOW) glycerol and a phase containing hydrophobic solvent and organic impurities. In one aspect, the process further includes the steps of subjecting a polar solvent to the DOW glycerol to produce a mixture of polar solvent and DOW glycerol and precipitating salt from the mixture of polar solvent and DOW glycerol; and separating the mixture of polar solvent and DOW glycerol into a light phase containing a deoiled, dewatered and desalted (DOWS) glycerol and the polar solvent and a heavy phase containing the salt.

Another aspect of the disclosure provides a process of producing partially refined waste glycerol by refining crude glycerol containing organic impurities, wherein the process includes drying the crude glycerol to produce a dewatered glycerol; subjecting a polar solvent to the dewatered glycerol to produce a mixture of polar solvent and dewatered glycerol and precipitating salt from the mixture of polar solvent and dewatered glycerol; and separating the mixture of polar solvent and dewatered glycerol into a light phase containing a dewatered and desalted glycerol and the polar solvent and a heavy phase containing the salt. In one aspect, the method further includes the steps of subjecting the dewatered and desalted glycerol to a hydrophobic solvent to produce a mixture of dewatered and desalted glycerol and hydrophobic solvent; and separating the mixture of dewatered and desalted glycerol and hydrophobic solvent to produce a dewatered, desalted, and deoiled (DOWS) glycerol and a phase containing hydrophobic solvent and organic impurities.

Another aspect of the disclosure provides a process of producing partially refined waste glycerol by refining crude glycerol containing organic impurities, wherein the process includes subjecting a polar solvent to the crude glycerol to produce a mixture of polar solvent and crude glycerol and precipitating a salt from the mixture of polar solvent and crude glycerol; and separating the mixture of polar solvent and crude glycerol into a light phase containing desalted glycerol and the polar solvent and a heavy phase containing the salt. In one aspect, the process further includes the steps of subjecting the desalted glycerol to a hydrophobic solvent to produce a mixture of desalted glycerol and hydrophobic solvent; and separating the mixture of desalted glycerol and hydrophobic solvent to produce a deoiled desalted glycerol and a phase containing hydrophobic solvent and organic impurities. In another aspect, the process further includes the step of drying the deoiled desalted glycerol to produce a desalted, deoiled, and dewatered (DOWS) glycerol.

The disclosure further contemplates a process of refining crude glycerol, including combining crude glycerol with a hydrophobic solvent to remove organic impurities and produce a deoiled (DO) glycerol; drying the DO glycerol to produce a deoiled and dewatered (DOW) glycerol; and subjecting a polar solvent to the DOW glycerol to precipitate salt and produce a deoiled, dewatered and desalted (DOWS) glycerol.

Another aspect of the disclosure provides a process of producing partially refined waste glycerol by refining crude glycerol containing organic impurities, wherein the process includes subjecting a crude glycerol to a hydrophobic solvent to produce a mixture of crude glycerol and hydrophobic solvent; separating the mixture of crude glycerol and hydrophobic solvent to produce a deoiled (DO) glycerol and a phase containing hydrophobic solvent and organic impurities; drying the DO glycerol to produce a deoiled and dewatered (DOW) glycerol; subjecting a polar solvent to the DOW glycerol to produce a mixture of polar solvent and DOW glycerol and precipitating a salt from the mixture of polar solvent and DOW glycerol; and separating the mixture of polar solvent and DOW glycerol into a light phase containing a deoiled, dewatered and desalted (DOWS) glycerol and the polar solvent and a heavy phase containing the salt. In another aspect, the process further includes partially evaporating the DOW glycerol before subjecting it to the polar solvent. In another aspect, the process further includes the step of evaporating the polar solvent from the DOWS glycerol to produce a purified DOWS glycerol. In one embodiment, the evaporation is flash evaporation. In one embodiment, the DOW glycerol has less than about 0.5 percent water. In another embodiment, the DOWS glycerol is a fermentation grade glycerol. In still another embodiment, the fermentation grade glycerol is salt-containing glycerol.

The disclosure further encompasses a process of refining crude glycerol, including combining crude glycerol with a hydrophobic solvent to remove organic impurities and create a deoiled (DO) glycerol; drying the DO glycerol to create a deoiled and dewatered (DOW) glycerol; partially evaporating about 75 percent of the DOW glycerol as a glycerol distillate without salt; recovering a remaining portion of said DOW glycerol in an evaporation discharge bottom; and adding a polar solvent to the evaporation discharge bottom to precipitate salt and create a deoiled, dewatered and desalted (DOWS) glycerol. In one embodiment, the polar solvent is IPA.

Another aspect of the disclosure provides a process of producing partially refined waste glycerol, including combining crude glycerol with a hydrophobic solvent to remove organic impurities and create a deoiled (DO) glycerol, wherein the DO glycerol encompasses partially refined waste glycerol. In one embodiment, the process further includes drying the DO glycerol to create a deoiled and dewatered (DOW) glycerol. In another embodiment, the process further includes adding a polar solvent to the DOW glycerol to precipitate salt and create a deoiled, dewatered and desalted (DOWS) glycerol. In one embodiment, the DOWS glycerol includes fermentation grade glycerol. In further embodiments, the order of the deoiling process steps, the dewatering process steps, and the desalting process steps differ from the above described process of DO→DOW→DOWS. In yet another embodiment, the hydrophobic solvent includes, but is not limited to, triacylglyceride, alkane, alkene, acetate, fatty acid alcohol ester. In one embodiment, the triacylglyceride is vegetable oil or fat. In another embodiment, the hydrophobic solvent is acetate. In another embodiment, the acetate is butyl acetate, or ethyl acetate. In yet another embodiment, the alkane is hexane. In still another embodiment, the organic impurities are oil-soluble. In another embodiment, the oil-soluble organic impurities are removed through liquid-liquid extraction with the hydrophobic solvent. In another embodiment, the DO glycerol includes less than about 195 ppm oil-soluble organic impurities. In another embodiment, the DOW glycerol includes less than about 0.5 percent water. In yet another embodiment, the polar solvent is an alcohol. In one embodiment, the polar solvent is isopropanol or butanol. In another embodiment, the salt is precipitated through extraction with the polar solvent. In another embodiment, the process further includes partial glycerol evaporation prior to the extraction with the polar solvent. In another embodiment, the process further includes evaporation of the polar solvent from the mixture of glycerol and solvent and desolventizing the wet precipitated salt. In one embodiment, the evaporation is flash evaporation. In another embodiment, the fermentation grade glycerol is salt-containing glycerol. In another embodiment, the fermentation grade glycerol includes a tailored salt content from about 0.05 to about 8.2 percent salt. In another embodiment, the fermentation grade glycerol includes a tailored salt content from about 0.05 to about 3.5 percent salt. In still another embodiment, the fermentation grade glycerol includes a tailored salt content from about 0.05 to about 2.0 percent salt. In one embodiment, the fermentation grade glycerol includes a tailored salt content from about 0.05 to about 1.0 percent salt.

Another aspect of the disclosure contemplates a partially refined waste glycerol derived from the processing of natural fats and oils, wherein the partially refined waste glycerol includes reduced salt and/or organic impurities as compared to crude glycerol. In one embodiment, the partially refined waste glycerol has a sodium chloride content. In another embodiment, the partially refined waste glycerol includes a sodium chloride content from about 0.05 percent to about 8.2 percent. In another embodiment, the partially refined waste glycerol includes a sodium chloride content from about 0.05 percent to about 3.5 percent. In another embodiment, the partially refined waste glycerol includes a sodium chloride content from about 0.05 percent to about 2.0 percent. In yet another embodiment, the partially refined waste glycerol includes a sodium chloride content from about 0.05 percent to about 1.0 percent. In still another embodiment, the partially refined waste glycerol is a fermentation grade glycerol.

Another aspect of the disclosure provides a process of refining crude glycerol, including: combining crude glycerol with a hydrophobic solvent to remove organic impurities and create a deoiled (DO) glycerol; drying the DO glycerol to create a deoiled and dewatered (DOW) glycerol; and adding a polar solvent to the DOW glycerol to precipitate salt and create a deoiled, dewatered and desalted (DOWS) glycerol. In one embodiment, the DO glycerol comprises partially refined waste glycerol. In another embodiment, the DOWS glycerol further includes fermentation grade glycerol. The hydrophobic solvent includes, but is not limited to, triacylglyceride, alkane, alkene, acetate, fatty acid alcohol ester, and the like. In one embodiment, the triacylglyceride is vegetable oil. In another embodiment, the acetate is butyl acetate. In another embodiment, the alkane is hexane. In yet another embodiment, the organic impurities are oil-soluble. In yet another embodiment, the oil-soluble organic impurities are removed through liquid-liquid extraction with the hydrophobic solvent. In one embodiment, the DO glycerol includes less than about 195 ppm oil-soluble organic impurities. In another embodiment, DOW glycerol includes less than about 0.5 percent water. In other embodiment, the polar solvent is an alcohol such as isopropanol or butanol. In another embodiment, the salt is precipitated through extraction with a polar solvent. In another embodiment, the process further includes partial glycerol evaporation prior to said extraction with said polar solvent. In still another embodiment, the process includes evaporation and desolventizing with said polar solvent. In a further embodiment, the process includes evaporation that is flash evaporation. In yet another embodiment, the fermentation grade glycerol is salt-containing glycerol.

The present disclosure further encompasses a process of refining crude glycerol, including: combining crude glycerol with a hydrophobic solvent to remove organic impurities and create a deoiled (DO) glycerol; drying the DO glycerol to create a deoiled and dewatered (DOW) glycerol; partially evaporating about 75 percent of the DOW glycerol as a glycerol distillate without salt; recovering a remaining portion of the DOW glycerol in an evaporation discharge bottom, wherein the remaining portion of the DOW glycerol is about 25 percent; and adding a polar solvent to said evaporation discharge bottom to precipitate salt and create a deoiled, dewatered and desalted (DOWS) glycerol. In one embodiment, the polar solvent is isopropyl alcohol (IPA).

Another aspect of the disclosure contemplates a process of producing or precipitating salt, including combining crude glycerol with a hydrophobic solvent to remove organic impurities and create a deoiled (DO) glycerol; drying the DO glycerol to create a deoiled and dewatered (DOW) glycerol; and adding a polar solvent to the DOW glycerol to precipitate salt and create a deoiled-, dewatered- and desalted (DOWS) glycerol, wherein the precipitated salt is produced as a by-product. The precipitated salt includes, but is not limited to, sodium chloride (NaCl), sodium sulfate ($Na_2SO_4$), sodium phosphate ($Na_3PO_4$), sodium nitrate ($NaNO_3$), sodium acetate ($C_2H_3NaO_2$), sodium carbonate ($Na_2CO_3$), sodium formate (HCOONa), sodium lactate ($C_3H_5NaO_3$), sodium gluconate ($C_6H_{11}NaO_7$), sodium citrate ($C_6H_5Na_3O_7$), sodium methanesulfonate ($CH_3NaO_3S$), potassium chloride (KCl), potassium sulfate ($K_2SO_4$), potassium phosphate ($K_3PO_4$), potassium nitrate ($KNO_3$), potassium acetate ($CH_3CO_2K$), potassium carbonate ($K_2CO_3$), potassium formate ($CHKO_2$), potassium lactate ($C_3H_5KO_3$), potassium gluconate ($C_6H_{11}KO_7$), potassium citrate ($C_6H_5K_3O_7$), and potassium methanesulfonate ($CH_3KO_3S$).

BRIEF DESCRIPTION OF THE DRAWINGS

The present disclosure is best understood when read in conjunction with the accompanying figures, which serve to illustrate the embodiments. It is understood, however, that the disclosure is not limited to the specific embodiments disclosed in the figures.

FIG. 2 depicts a block diagram of a production cycle for making partially refined waste glycerol, including salt-containing fermentation grade glycerol, wherein the steps encompass deoiling, dewatering and desalting glycerol. The process includes hydrophobic solvent liquid-liquid extraction through the use of triacylglycerides (TAG); moisture drying; polar solvent extraction, polar solvent evaporation, and polar solvent desolventizing. Isopropanol (IPA) is shown as the polar solvent, which is reused in this process.

FIG. 3 depicts a block diagram of a production cycle for making partially refined waste glycerol, including salt-containing fermentation grade glycerol, wherein the steps encompass deoiling, dewatering and desalting glycerol. The process includes hydrophobic solvent liquid-liquid extraction through the use of alkanes, alkenes, alcohol esters or acetates (hexane is shown here), wherein the hydrophobic solvent is evaporated (e.g., through flash evaporation) and reused; moisture drying, polar solvent extraction, polar solvent evaporation, and polar solvent desolventizing. IPA is shown as the polar solvent, which is reused in this process.

FIG. 4 depicts a block diagram of a production cycle for making partially refined waste glycerol, including salt-containing fermentation grade glycerol, wherein the steps encompass deoiling, dewatering and desalting glycerol. The process is a hybrid process that includes hydrophobic solvent liquid-liquid extraction through the use of triacylglycerides (TAG), moisture drying, optional glycerol evaporation, polar solvent extraction, polar solvent evaporation, and polar solvent desolventizing. Here, glycerol is optionally evaporated to reduce processing volume in the polar solvent extraction step before the polar solvent is added. IPA is shown as the polar solvent, which is reused in this process.

FIG. 5 depicts a block diagram of a production cycle for making partially refined waste glycerol, including salt-containing fermentation grade glycerol, wherein the steps encompass deoiling, dewatering and desalting glycerol. The process is a hybrid process that includes hydrophobic solvent liquid-liquid extraction through the use of alkanes, alkenes, or acetate (hexane is shown here), wherein the hydrophobic solvent is evaporated (e.g., through flash evaporation) and re-used; moisture drying, optional glycerol evaporation, polar solvent extraction, polar solvent evaporation, and polar solvent desolventizing. Here, glycerol is optionally evaporated before the polar solvent is added. IPA is shown as the polar solvent, which is reused in this process.

FIG. 6 depicts a graph that shows an IPA to glycerol ratio per weight (IPA:glycerol) vs. the salt concentration of NaCl that remains in the resulting DOWS glycerol.

DETAILED DESCRIPTION

Brief Overview

Figure 1A:
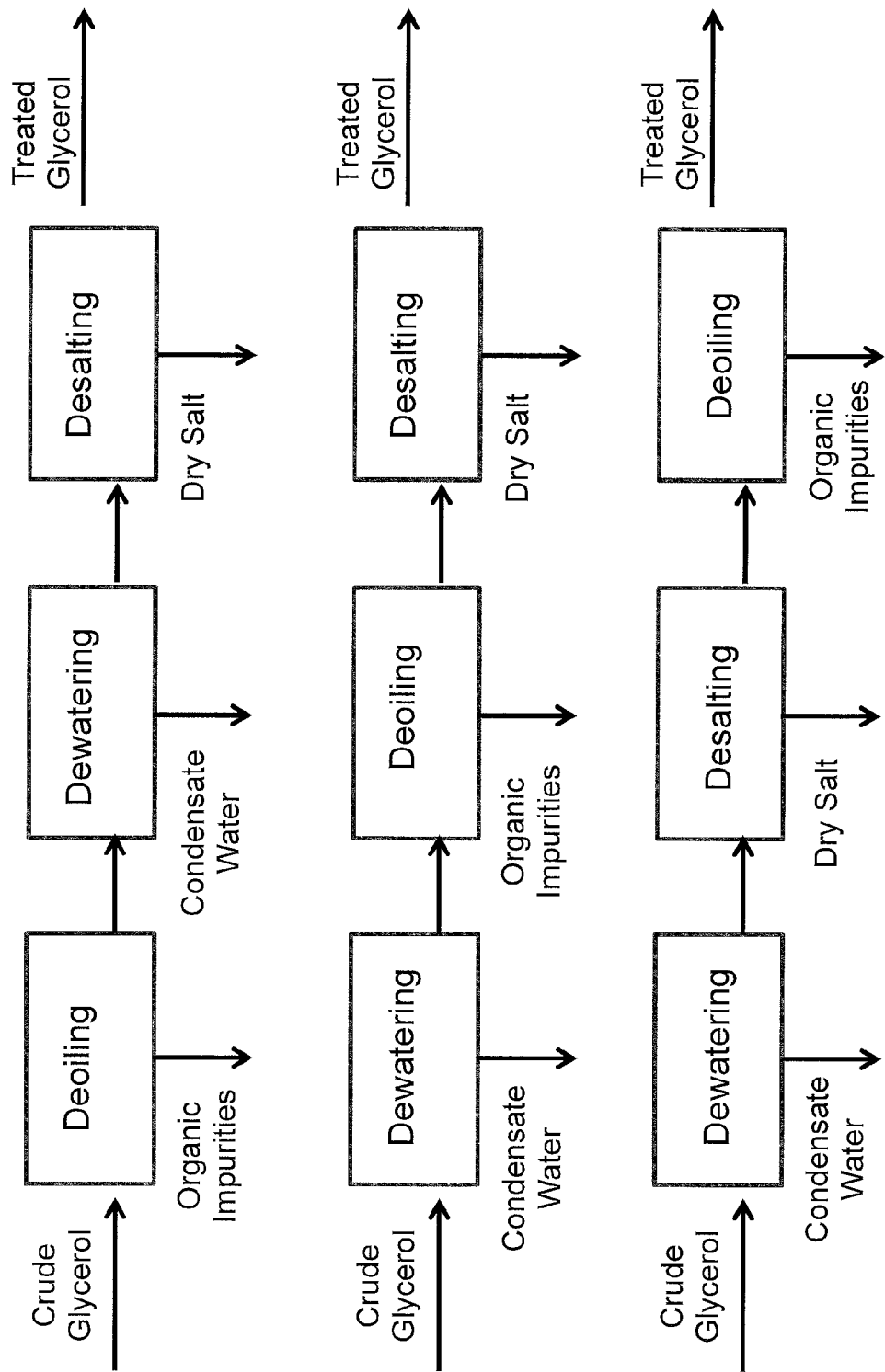
FIGS. 1A and 1B depict block flow diagrams showing five differing embodiments of the process for producing partially refined waste glycerol from crude glycerol.

The disclosure provides an efficient and cost-effective process to produce partially refined waste glycerol, including salt-containing fermentation grade glycerol. In an industrial setting, glycerol is a by-product of biodiesel production and other fat-splitting processes that include methods for making bio-fuels and bio-hydrocarbons. Crude glycerol derived from biodiesel and fat-splitting processes has organic impurities (i.e., oil-soluble and water-soluble impurities) as well as inorganic impurities such as salts including sodium chloride (NaCl), potassium chloride (KCl), sodium sulfate ($Na_2SO_4$), potassium sulfate ($K_2SO_4$) and others; heavy metals; and inorganic boiler chemicals depending on the source of the glycerol and the process employed. The impurities in crude glycerol as a source material or feedstock can affect performance of any particular end product in industrial applications. For fermentation applications, the performance includes yield, productivity and titer. Thus, the present disclosure provides a process of purifying crude glycerol where organic and inorganic impurities in glycerol are substantially reduced without yet meeting the purity standard of USP glycerol, resulting in partially refined waste glycerol, including salt-containing fermentation grade glycerol, which can be used in many industrial applications.

DEFINITIONS

The terms "glycerol" and "glycerin" and "glycerine" are used interchangeably herein and refer to a molecule that is covered by the chemical formula $CH_2(OH)CH(OH)$ $CH_2OH$. Glycerol is also referred to as a trihydric alcohol; propane-1,2,3-triol; 1,2,3-propanetriol; 1,2,3-trihydroxypropane; glyceritol; glycerine; and/or glycyl alcohol, all of which are encompassed herein.

The term "crude glycerol" refers to a substance that is composed of mostly glycerol and impurities, including but not limited to, methanol, water, both polar and non-polar organics and/or salts. In one embodiment, crude glycerol contains methanol, water, soaps, and salts and has a glycerol content of about 40 to about 89 percent. In another embodiment, crude glycerol as starting material contains about 0 to about 90% water, salts and/or organic materials. In another embodiment, crude glycerol is a by-product of a transesterification process. In still another embodiment, crude glycerol is a by-product from the manufacture of biodiesel. Crude glycerol derived from the manufacture of biodiesel contains between about 70% to about 80% triglycerides and between about 20% to about 30% total impurities including organic and inorganic impurities (see, e.g., Table 1A). In another embodiment, crude glycerol is a by-product of a fat-splitting process. In another embodiment, crude glycerol is a by-product of a soup making process.

A "partially refined waste glycerol" refers to a glycerol that is produced by the purification process described herein. In some embodiments, it is derived from the processing of natural fats and oils. In other embodiments, it encompasses reduced salt and reduced organic impurities as compared to crude glycerol. As such, it may typically contain trace levels of oil-soluble organic impurities and salts (e.g., NaCl, KCl, $Na_2SO_4$, $K_2SO_4$, etc.) and may have a purity standard that ranges from about 90 percent to about 99 percent, more commonly from about 95 percent to about 99 percent, and most commonly from about 97 percent to about 99 percent, depending on salt concentration. The salt concentration in partially refined waste glycerol may range from 0 percent to about 8.2 percent. In one embodiment, salt-containing partially refined waste glycerol contains NaCl or KCl or $Na_2SO_4$ or $K_2SO_4$ or a combination thereof. In another embodiment, salt-containing partially refined waste glycerol contains NaCl or KCl or $Na_2SO_4$ or $K_2SO_4$ or sometimes more than one of these salts or any other salt(s) that result from neutralizing of a homogeneous base catalyst used in a biodiesel reaction with acid(s). The base catalysts may be monovalent cationic oxides (e.g., $Na_2O$, $K_2O$), cationic hydroxides (e.g., NaOH, KOH), and/or cationic methylates and ethylates (e.g., $NaOCH_3$, $NaOC_2H_5$, $KOCH_3$, $KOC_2H_5$) that are soluble in a biodiesel reaction mixture. The acid(s) may be either inorganic or organic acid(s). Examples of inorganic acid(s) are HCl, $SO_3$, $H_2SO_4$, $H_3PO_4$, $HNO_3$, and others. Examples of organic acids are $H_2CO_3$, acetic acid, formic acid, lactic acid, gluconic acid, citric acid, succinic acid, and others. Examples of the resulting salts are listed in Table 1B (infra). Partially refined waste glycerol is suitable as an aid or component in many industrial and/or commercial applications including, but not limited to, paints, coats, adhesives, textiles, woods, metals, detergents, soaps, coolants, cleaners, paper, and others.

A "fermentation grade glycerol" is an example of a salt-containing partially refined waste glycerol that has a specific salt content that ranges from about 0.05 percent salt to less than about 8.2 percent salt (e.g., NaCl, KCl, $Na_2SO_4$, $K_2SO_4$) and more particularly, from about 0.05 percent salt to about 2.0 percent salt. Typically, fermentation grade glycerol contains mostly NaCl or KCl or $Na_2SO_4$ or $K_2SO_4$ or sometimes more than one of these salts or other salts (see Table 1B, infra) or combinations of other salts (see Table 1B, infra). Fermentation grade glycerol is particularly suitable as a feedstock for fermentation procedures. Herein, fermentation grade glycerol is suitable for a wide variety of microbes that are employed in fermentation cultures as production hosts. Examples of such microbial hosts include, but are not limited to organisms from the genus *Escherichia, Bacillus, Lactobacillus, Rhodococcus, Synechococcus, Synechoystis, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia,* or *Streptomyces*. In one embodiment, the microbial host is *Escherichia coli*. In other embodiments, the microbial host is *Bacillus lentus, Bacillus brevis, Bacillus stearothermophilus, Bacillus licheniformis, Bacillus alkalophilus, Bacillus coagulans, Bacillus circulans, Bacillus pumilis, Bacillus thuringiensis, Bacillus clausii, Bacillus megaterium, Bacillus subtilis,* and/or *Bacillus amyloliquefaciens*. In other embodiments, the microbial host is *Synechococcus* sp. PCC7002, *Synechococcus elongatus* PCC 7942, *Synechoystis* sp. PCC 6803, *Synechococcus elongatus* PCC6301, *Prochlorococcus marinus* CCMP1986 (MED4), *Anabaena variabilis* ATCC29413, *Nostoc punctiforme* ATCC29133 (PCC73102), *Gloeobacter violaceus* ATCC29082 (PCC7421), *Nostoc* sp. ATCC27893 (PCC7120), *Cyanothece* sp. PCC7425 (29141), *Cyanothece* sp. ATCC51442, and/or *Synechococcus* sp. ATCC27264 (PCC7002). In other embodiments, the microbial host is *Trichoderma koningii, Trichoderma viride, Trichoderma reesei, Trichoderma longibrachiatum, Aspergillus awamori, Aspergillus fumigates, Aspergillus foetidus, Aspergillus nidulans, Aspergillus niger, Aspergillus oryzae, Humicola insolens, Humicola lanuginose, Rhodococcus opacus, Rhizomucor miehei,* and/or *Mucor michei*. In other embodiments, the microbial host is *Actinomycetes*. In yet other embodiments, the microbial host is *Streptomyces lividans* and/or *Streptomyces murinus*. In other embodiments, the microbial host is *Saccharomyces cerevisiae*.

The term "hydrophobic solvent" refers to a compound that does not mix with water and readily partitions and/or is miscible with a substance having hydrophobic characteristics. Examples of a hydrophobic solvent include, but are not limited to, acetates (e.g., butyl acetate, ethyl acetate), fatty acid alcohol esters (e.g., fatty acid methyl ester (FAME), fatty acid ethyl ester (FAEE), and fatty acid isopropyl ester), triacylglycerides (e.g., vegetable oil), alkanes (e.g., hexane, isohexane, and octane), and alkenes (e.g., hexene, and octene).

The term "polar solvent" means, for the purpose of the specification and claims, a compound that is readily miscible with glycerol, can solubilize salt to only low levels if at all, and has a lower boiling point than glycerol. Examples of such polar solvents are alcohols, including but not limited to, isopropanol or isopropyl alcohol (IPA), 1-propanol, 1-butanol, 2-butanol, tert-butanol, ethanol, and methanol. Another example of a polar solvent is phenol.

The term "DO glycerol" means, for the purpose of the specification and claims, a form of glycerol that has been partially refined by virtue of deoiling it. In one embodiment, DO glycerol contains fewer oil-soluble organic impurities than crude glycerol, i.e., oil-soluble organic impurities have been mostly removed and are present below than about 195 ppm.

The term "DOW glycerol" means, for the purpose of the specification and claims, a form of glycerol that has been deoiled and dewatered in any order. DOW glycerol is the result of drying DO glycerol such that most of the water has been removed. In one embodiment, DOW glycerol contains less than about 0.5 percent water.

The term "DOWS glycerol" means, for the purpose of the specification and claims, a form of glycerol that has been deoiled, dewatered, and desalted in any order. DOWS glycerol is the result of desalting DOW glycerol such that most of the salt has been removed. In one embodiment, DOWS glycerol for fermentation application contains about 0.05 percent to about 2.0 percent salt.

Glycerol

Glycerol is a trihydric alcohol, i.e., it is made up of three alcohol groups. The chemical structure of glycerol is $CH_2(OH)CH(OH)CH_2OH$. It is a clear, odorless, viscous liquid with a naturally sweet taste. The terms glycerol and glycerin are often used interchangeable, although glycerol is the principle component of glycerin, e.g., about 96 percent glycerol may be glycerin. Glycerol has a high boiling point and can be dissolved by water and alcohol but not usually by oils. Crude glycerol is a natural by-product from the processing of fats and oils. For example, it is produced during transesterification of biodiesel production processes (supra). In comparison, USP Grade Glycerol (USP glycerol) is considered a pharmaceutical grade glycerol that is highly pure. The abbreviation USP stands for United States Pharmacopeia (i.e., a document that was first published in 1820 and used as a standard reference by physicians). Today, the USP includes chemical descriptions, identifying tests, and purity tests for mostly active ingredients. All materials listed in the USP are considered subject to the U.S. Food and Drug Administration (FDA) requirements. Thus, labeling a product or a substance as USP, as in USP glycerol, implies that it conforms to the requirements of the FDA. USP glycerol has to meet specific purity guidelines because it is used for pharmaceuticals, foods, personal care, cosmetics, fragrances and other specialty applications. The composition for USP glycerol on a dry basis must meet a 99.7 to 100 percent purity standard and any trace amounts of impurities must meet the USP specifications. This is a high standard for a product and reflected in the cost of production. USP grade glycerol is primarily produced by fractional distillation (supra). Another category of glycerol is technical grade glycerol, which must not meet the same purity standards as USP grade glycerol but it must be cleaner than crude glycerol in order for it to be suitable for use in industrial products (e.g., paints, coats, gels, adhesives, etc.). Technical grade glycerol is typically purified (e.g., about 80 to about 97 percent pure) with most of its contaminants removed (i.e., no methanol, no soaps, no salts, etc.). As a result, technical grade glycerol is expensive to make because similar to USP grade glycerol, it is primarily produced by fractional distillation (supra).

Partially Refined Waste Glycerol

The present disclosure provides a new form of glycerol, such as a partially refined waste glycerol. Partially refined waste glycerol has a novel composition that is cleaner than crude glycerol but is not as highly purified as USP glycerol or technical grade glycerol, in particular, it can contain trace levels of oil-soluble organic impurities and/or salt. In one embodiment, a partially refined waste glycerol contains some salt. In another embodiment, a partially refined waste glycerol is salt free. In another embodiment, partially refined waste glycerol can encompass a tailored salt concentration that is adjusted to the use of the glycerol product. In one embodiment, partially refined waste glycerol is cleaner than crude glycerol but contains trace levels of oil-soluble organic impurities. In another embodiment, partially refined waste glycerol is cleaner than crude glycerol but contains trace levels of oil-soluble organic impurities and salt. In yet another embodiment, partially refined waste glycerol is cleaner than crude glycerol but contains salt. In one embodiment, partially refined waste glycerol has a salt concentration of 0 percent to about 8.2 percent. Fermentation grade glycerol is an example of partially refined waste glycerol. In one embodiment, fermentation glycerol has a salt concentration of about 0.05 percent to less than about 8.2 percent, including from about 0.05 percent to about 2.0 percent. In another embodiment, fermentation grade glycerol that is particularly suitable for the use in fermentation cultures where living organisms are used as production hosts (see, e.g., U.S. Pat. Nos. 8,372,610; 8,323,924; 8,313,934; 8,283,143; 8,268,599; 8,183,028; 8,110,670; 8,110,093; and 8,097,439, all of which are incorporated herein by reference).

Fermentation Grade Glycerol

Fermentation grade glycerol is an example of partially refined waste glycerol, where the salt content of the glycerol composition can be tailored to the need of the organism that is used in a fermentation method. Microorganisms can be used as production hosts in fermentation cultures in order to produce desired chemicals (e.g., fatty acids, fatty alcohols, fatty esters, fatty alkanes, fatty alkenes, organic acids, diacids, terpenoids, monomers, polymers, and others). These microorganisms or host cells use a carbon source or feedstock as a form of food and energy (e.g., host cells that produce fatty acid derivatives during a fermentation process when a carbon source including glycerol is used as a feedstock, see, e.g., U.S. Pat. Nos. 8,372,610; 8,323,924; 8,313,934; 8,283,143; 8,268,599; 8,183,028; 8,110,670; 8,110,093; and 8,097,439, all of which are incorporated herein by reference).

In a natural environment, each microorganism has a certain set tolerance for salt, i.e., each microorganism requires a particular level of salt in order to satisfy its mineral nutrient requirements (e.g., sodium chloride, phosphates, etc.). Nature generally supplies enough salt to microbes. Conversely, if salt levels are too high they become toxic and the microorganism eventually turns inactive or dies. Biodiesel crude glycerol has a salt content of about 6 to 8 percent, which exceeds the tolerance level of many microorganisms. Thus, when the salt content of glycerol as a feedstock in a fermentation broth is too high the microbes become inactive. This explains why microbes that are used in fermentations are generally fed with feedstock that meets a higher purity standard or does not normally contain high salt or other impurities (e.g., corn syrup, cane juice, USP glycerol, etc). Conversely, when the salt content of glycerol as a feedstock in a fermentation broth is too low (i.e., it falls below a certain level) the microbes can no longer function as efficiently. For example, marine organisms grow well at about 3.5 percent salt in a fermentation broth while *E. coli* prefer about 0.5 to about 1.0 percent and generally tolerate no more than about 2 percent in a fermentation broth. Raising the salt concentration of a fermentation broth can increase the productivity of the microbes to levels that are expected. This is typically accomplished by adding extra salt during the fermentation run as needed, because when glycerol is used as a feedstock it is usually a high purity glycerol that cannot itself contribute to the salt content. However, when fermentation glycerol was used it was unnecessary to add additional salt to the fermentation broth (see Examples, Tables 3 and 4 (infra) and FIG. 6). Without wanting to the bound by theory, it is suggested that fermentation grade glycerol may be well tolerated because it supplies the microorganisms with just the right amount of salt they need in order to function optimally. It is well known that microorganisms can grow in a broad range of salt concentrations, but the majority of microorganisms that have industrial significance require a certain osmolarity in the growth media, which is mostly provided by the addition of salts. The beneficial osmolarity range is in general between about 25 to about 500 mOsmol per liter (mOsmol/L). Any fermentation that uses microorganisms that require salt for optimal performance would benefit from fermentation grade glycerol because it is neither too toxic nor completely devoid of salt. Thus, a fermentation grade glycerol is desirable, particularly a composition where the salt content can be tailored to the need of the specific microorganism in culture.

In one embodiment, the present disclosure provides a glycerol composition that is a fermentation grade glycerol composition with a tailored salt content. In another embodiment, the present disclosure provides a fermentation grade glycerol composition that includes a tailored salt content that ranges from about 0.05 percent to about 2 percent salt content. In another embodiment, the present disclosure provides a fermentation grade glycerol composition that includes a tailored salt content that ranges from about 0.06 percent to about 2 percent salt content. In another embodiment, the present disclosure provides a fermentation grade glycerol composition that includes a tailored salt content that ranges from about 0.07 percent to about 2 percent salt content. In yet another embodiment, the present disclosure provides a fermentation grade glycerol composition that includes a tailored salt content that ranges from about 0.08 percent to about 2 percent salt content. In still another embodiment, the present disclosure provides a fermentation grade glycerol composition that includes a tailored salt content that ranges from about 0.09 percent to about 2 percent salt content. In another embodiment, the present disclosure provides a fermentation grade glycerol composition that includes a tailored salt content that ranges from about 0.1 percent to about 2 percent salt content. In further embodiments, the present disclosure provides a fermentation grade glycerol composition that includes, but is not limited to, a tailored salt content that ranges from about 0.2 percent to about 2 percent salt content; from about 0.3 percent to about 2 percent salt content; from about 0.4 percent to about 2 percent salt content; from about 0.5 percent to about 2 percent salt content; from about 0.6 percent to about 2 percent salt content; from about 0.7 percent to about 2 percent salt content; from about 0.8 percent to about 2 percent salt content; from about 0.9 percent to about 2 percent salt content; from about 1 percent to about 2 percent salt content; and from about 1.1 percent to about 2 percent salt content. In further embodiments, the present disclosure provides a fermentation grade glycerol composition that includes, but is not limited to, a tailored salt content that ranges from about 1.2 percent to about 2 percent salt content; from about 1.3 percent to about 2 percent salt content; from about 1.4 percent to about 2 percent salt content; from about 1.5 percent to about 2 percent salt content; from about 1.6 percent to about 2 percent salt content; from about 1.7 percent to about 2 percent salt content; from about 1.8 percent to about 2 percent salt content; and from about 1.9 percent to about 2 percent salt content. In a separate embodiment, the present disclosure provides a fermentation grade glycerol composition that includes a tailored salt content that ranges from about 0.05 percent to less than about 8.2 percent salt content. In another embodiment, the present disclosure provides a fermentation grade glycerol composition that includes, but is not limited to, a tailored salt content that ranges from about 0.05 percent to about 3.5 percent salt content; from about 0.05 to about 3 percent salt content; from about 0.05 to about 2.8 percent salt content; and from about 0.05 to about 2.5 percent salt content.

In many industrial applications (i.e., where USP glycerol is currently used because crude glycerol is not clean enough), an alternative version of a cleaner glycerol would be desirable because the purity standard does not necessarily have to be close to 99 percent. Partially refined waste glycerol, including fermentation grade glycerol can meet the 90 to 99 percent purity standard that is desirable for many industrial applications while being produced at a much lower cost. Typically, partially refined waste glycerol has a purity of about 90 percent to about 99 percent (e.g., about 91 percent to about 99 percent, about 92 percent to about 99 percent, about 93 percent to about 99 percent, about 94 percent to about 99 percent, about 95 percent to about 99 percent, about 96 percent to about 99 percent, or about 97 percent to about 99 percent, or about 98 percent to about 99 percent), depending on salt concentration and water content. Allowing higher amounts of crude glycerol to be converted to partially refined waste glycerol including fermentation grade glycerol may prevent a surplus of crude glycerol on the world market since higher amounts of crude glycerol are expected to be produced with the rise of biodiesel products. It may further eliminate the high cost of toxic waste disposal for crude glycerol and may create a new profit margin for biodiesel plant owners.

Glycerol in Fermentation

Fermentation procedures employ living organisms that cannot survive under toxic conditions. The fermentation environment has to be adjusted to support the growth of the microbes in culture. Since glycerol is used as a feedstock in fermentation procedures it must be suitable for microbial consumption and should be mostly free of toxic by-products. The present disclosure provides a process for glycerol purification or refinement that includes organic extraction and salt precipitation, where toxic impurities in glycerol are reduced to support microbial growth while still leaving enough salt for the microbes to thrive. In one embodiment, the process allows for removal of oil-soluble organic impurities from glycerol. In another embodiment, the process allows for removal of some inorganic impurities from glycerol. In one embodiment, impurities are removed through an extraction or deoiling technique by using a hydrophobic solvent such as, for example, an acetate (e.g., butyl acetate, ethyl acetate), a fatty acid alcohol ester (e.g., fatty acid methyl ester (FAME), fatty acid ethyl ester (FAEE), and fatty acid isopropyl ester), a triacylglyceride (TAG) (e.g., vegetable oil), an alkane (e.g., hexane, isohexane, and octane), an alkene (e.g., hexene, and octene) or the like. As a result, the toxicity of glycerol is substantially reduced and any potential contamination during fermentation is minimized. The extraction of impurities as described herein may be a high-throughput process that functions in a low cost operating environment.

In another embodiment, the process allows for fine-tuning the salt content in glycerol in order to produce partially refined waste glycerol, including fermentation grade glycerol. As such, the process allows for tailoring the final salt content in the glycerol composition as an end product. The ability to tailor the salt content of partially refined waste glycerol is desirable because each microorganism in a fermentation broth has a certain set tolerance for salt, i.e., if the salt concentration in the broth becomes too high the microorganism may eventually become inactive and die (supra). Conversely, each microorganism may require a certain level of salt in order to satisfy its mineral nutrient requirements and grow optimally in a fermentation broth. Thus, if the salt content in glycerol as a feedstock is too high or too low then the microorganism can no longer function properly (e.g., microbial hosts that produce fatty acid derivatives during a fermentation process when glycerol is used as a feedstock, see, e.g., U.S. Pat. Nos. 8,372,610; 8,323,924; 8,313,934; 8,283,143; 8,268,599; 8,183,028; 8,110,670; 8,110,093; and 8,097,439, all of which are incorporated herein by reference). In one embodiment, the salt content in fermentation grade glycerol is adjusted to be between about 0.05 and less than about 8.2 percent in a fermentation broth, which may benefit microbial organisms that are used as hosts in fermentation cultures. In one embodiment, the salt content in fermentation grade glycerol is adjusted to be between about 0.05 and about 2.0 percent in a fermentation broth, which may benefit microbial organisms that are used as hosts for production in fermentation cultures. In another embodiment, the salt content in fermentation grade glycerol is adjusted to be between about 0.05 and about 1.0 percent in a fermentation broth, which may benefit microbial organisms that are used as hosts for production in fermentation cultures. In yet another embodiment, the salt content in fermentation glycerol is adjusted to be between about 0.05 and about 3.5 percent in a fermentation broth.

In one embodiment, the present method can reduce the salt level (e.g., NaCl, KCl, $Na_2SO_4$, $K_2SO_4$) in crude glycerol by precipitating the existing salt using an alcohol (e.g., isopropyl alcohol (IPA), 1-pantanol, 1-butanol, etc.), followed by evaporation of alcohol; and then fine-tune the salt level in fermentation grade glycerol by further extraction and evaporation. Herein the salt removal can be controlled and specifically tailored to the specific microorganism and based on the desired end product (i.e., various fermentation grade glycerol compositions having a certain salt content). The desalting and evaporation steps may be part of the high throughput processing, adding to the overall low operating cost of this method. Hence, fermentation grade glycerol with its tailored salt content and reduced oil-soluble organic impurities can be made from crude glycerol following the specific processing steps (i.e., deoiling, dewatering and desalting steps) as discussed herein (infra).

In another embodiment, crude glycerol contains about 0.1 percent to about 3 percent of organic impurities overall; about 7 percent to about 9 percent of salt (e.g., on a dry basis, from a biodiesel process) or about 3 percent of salt (e.g., on a dry basis, from a fat-splitting process); and trace levels of heavy metals. Table 1A below shows an example of a crude glycerol composition (as a by-product of a biodiesel production) with its organic and inorganic contaminants and impurities. Most of the impurities listed in Table 1A have a higher boiling point than glycerol. Some of them, such as 3-monochloropropane-1,2-diol (3-MPCD), which is an organic boiler chemical, have a boiling point similar to glycerol. Organic and inorganic acids as well as methanol and low molecular weight diacetyl ketone (DAK) have lower boiling points than glycerol and water.

TABLE 1A

Example of a Crude Glycerol Composition

| Type | Potential Contaminants and Impurities in Crude Glycerol derived from Biodiesel |
|---|---|
| Organics | |
| | Methanol |
| | Monoacylglycerides (MAG), Diacylglycerides (DAG), Triacylglycerides (TAG) and Free Fatty Acids (FFA) |
| | Fatty Acid Methyl Esters (FAME) |
| | Poly-Aromatic Hydrocarbons (PAH) |
| | Dioxins And Dioxin Like Poly-Chlorinated Biphenyl (PCBS) |
| | Mycotoxins, |
| | Diacetyl Ketone (DAK) |
| | Pesticides |
| | 3-Monochloropropane-1,2-Diol (3-MPCD) |
| | Mineral Oils |
| | Organic Boiler Chemicals |
| Inorganics | |
| | Salt (e.g., NaCl, $Na_2SO_4$, KCl, $K_2SO_4$, sodium acetate, potassium acetate, etc.) |
| | Heavy Metals |
| | Inorganic Boiler Chemicals |

The salt content in crude glycerol (e.g., about 3 to about 9 percent) exceeds the salt tolerance of many living microorganisms. In addition, crude glycerol contains contaminants and impurities, including heavy metals (see Table 1A, supra). Hence, crude glycerol is not suitable as feedstock for most industrial microbial hosts. For example, if crude glycerol is fed to *E. coli* in a fermentation broth that produces fatty acid methyl esters (FAME) *E. coli* activity ceases within 48 hours (see Table 4, infra). Conversely, when oil soluble organic impurities and salts are reduced and the cleaner fermentation grade glycerol is used as feedstock, the performance of fermentation improved (see Table 4, infra). This shows that the levels of oil-soluble organic impurities and salt in glycerol can affect fermentation performance of living organisms when glycerol is used as feedstock. In one embodiment, glycerol contains about 1 to about 2 percent of salt so that good recovery of product can be achieved via a fermentation culture. For example, when glycerol contained about 1 percent of salt, ester production via *E. coli* in culture was noticeably improved (see Table 3 and Example 10, infra).

In many microbial organisms, growth starts to be inhibited at salt concentrations above 2 percent, and growth inhibition is more or less affected depending on the microbe, the additional media components and the environmental conditions. Marine organisms (halophiles) are exceptions and are able to grow in salt concentrations above that of sea water (about 3.5 percent). In one embodiment, when glycerol contains about 2 to 3 percent of salt, fatty acid derivative production via halophiles in culture would be improved. Some microbes can grow at salt concentrations up to 20 to 25 percent, although such a high salt content would not be suitable for most industrial applications and/or fermentation cultures.

Process of Producing Partially Refined Waste Glycerol

The disclosure provides a new and clean process for producing high yields of partially refined waste glycerol at a minimum cost to the environment. The process entails organic extraction and salt precipitation. The aim of this new process is to produce partially refined waste glycerol that can be used in various industrial applications including, for example, chemical production via fermentation, animal feeds, green automobile coolants, and the like. One advantage of this process is that partially refined waste glycerol is produced in a high-throughput capacity, which is less expensive than conventional fractional distillation methods (supra). Another advantage of this process is that it creates fewer waste products because it proceeds with a relatively minor loss of glycerol and reuses hydrophobic and polar solvents, thereby reducing the impact on the environment. FIGS. 1 through 5 depict flow diagrams of the process of producing partially refined waste glycerol. In one embodiment, the process may be carried out via mixing tanks, liquid-liquid separators, and desolventizers as known in the art. In another embodiment, the process includes hydrophobic solvent liquid-liquid extraction through the use of a hydrophobic solvent such as, for example, triacylglycerides (TAG), moisture drying, polar solvent extraction, polar solvent evaporation, and polar solvent desolventizing (see FIG. 2). In another embodiment, the process includes hydrophobic solvent liquid-liquid extraction through the use of a hydrophobic solvent such as, for example, butyl acetate, moisture drying, polar solvent extraction, polar solvent evaporation, and polar solvent desolventizing. In another embodiment, the process includes hydrophobic solvent liquid-liquid extraction through the use of a hydrophobic solvent such as, for example, FAME, moisture drying, polar solvent extraction, polar solvent evaporation, and polar solvent desolventizing. In another embodiment, the process includes hydrophobic solvent liquid-liquid extraction through the use of alkanes (e.g., hexane) or alkenes (e.g., hexene) or acetates (e.g., butyl acetate, ethyl acetate), wherein the hydrophobic solvent is evaporated (e.g., through flash evaporation) and re-used; moisture drying, polar solvent extraction, polar solvent evaporation, and polar solvent desolventizing (see FIG. 3). In another embodiment, the process includes hydrophobic solvent liquid-liquid extraction through the use of a hydrophobic solvent (e.g., triacylglycerides (TAG)), moisture drying, optional glycerol evaporation, polar solvent extraction, polar solvent evaporation, and polar solvent desolventizing (see FIG. 4). Herein, glycerol is optionally evaporated before the polar solvent is added. In another embodiment, the process includes hydrophobic solvent liquid-liquid extraction through the use of alkanes (e.g., hexane) or alkenes (e.g., hexene) or acetate (e.g., ethyl acetate) or fatty acid alcohol esters (e.g. FAME, FAEE and fatty acid isoprophyl esters), wherein the hydrophobic solvent is evaporated (e.g., through flash evaporation) and re-used; moisture drying, optional glycerol evaporation, polar solvent extraction, polar solvent evaporation, and polar solvent desolventizing (see FIG. 5). Similarly, glycerol is optionally evaporated before the polar solvent is added. As can be seen in FIGS. 3 and 5, hydrophobic solvent evaporation allows for the reuse of the solvent back into the system and further separates out oil-soluble organic impurities. In one embodiment, the hydrophobic solvent is TAG. In another embodiment the hydrophobic solvent is hexane. In another embodiment, the polar solvent is isopropanol (IPA), which can be reused in this process.

In order to utilize crude glycerol (e.g., from biodiesel and fat-splitting processes) and produce partially refined waste glycerol, crude glycerol can be deoiled, dewatered and desalted in any order. In the flow diagrams of FIGS. 2-5, deoiling glycerol encompasses hydrophobic solvent liquid-liquid extraction; dewatering glycerol encompasses moisture drying; and desalting glycerol encompasses optional glycerol evaporation, polar solvent extraction, polar solvent evaporation, and polar solvent desolventizing. Since both hydrophobic and polar solvents can be reused in this system not much waste product is generated. There is minor loss of glycerol and the process can be carried out in a biodiesel facility by using triacylglycerides (TAG), butyl acetate, ethyl acetate, FAME, FAEE, fatty acid isopropyl ester, hexane, or the like as a hydrophobic solvent. In addition, any oil-soluble or organic impurities can be reused as boiler fuel. Hence, the process is recyclable, cost effective, and green.

More specifically, two interchangeable process routes were developed to treat crude glycerol in order to produce partially refined waste glycerol, including salt-containing fermentation grade glycerol. The first process route includes deoiling crude glycerol through a hydrophobic solvent liquid-liquid extraction step (e.g., via TAG, butyl acetate, ethyl acetate, FAME, FAEE, fatty acid isopropyl ester or hexane) and dewatering the deoiled glycerol through moisture drying. The deoiled and dewatered glycerol undergoes desalting through a polar solvent-based salt precipitation step (e.g., via IPA) (see FIGS. 2 and 4). The ordering of the basic process steps of deoiling, dewatering, and desalting is interchangeable (see FIGS. 1A and 1B). The second process route includes deoiling crude glycerol through a hydrophobic or hydrophobic solvent liquid-liquid extraction step (e.g., via TAG, butyl acetate, ethyl acetate, FAME, FAEE, fatty acid isopropyl ester or hexane), dewatering the deoiled glycerol through moisture drying; and evaporating the deoiled and dewatered glycerol, followed by a polar solvent-based salt precipitation step (e.g., via IPA) of the evaporation bottom (see FIGS. 3 and 5). Similarly, the ordering of the basic process steps of deoiling, dewatering, and desalting is interchangeable (see FIGS. 1A and 1B). Both process routes result in partially refined waste glycerol that has fewer oil soluble organic impurities and a lower salt content then crude glycerol. The salt concentration of the final glycerol product can be tailored to produce a partially refined waste glycerol that contains a desirable concentration of salt, making it a suitable feedstock for many industrial applications including fermentation. In addition, the salt content of partially refined waste glycerol can be fine-tuned, resulting in a particularly suitable feedstock for fermentation (i.e., fermentation grade glycerol) that requires a specific salt-content due to its production hosts. In one embodiment, salt reduction, salt tailoring and/or salt fine-tuning can be achieved by employing both process routes. Thus, both process routes can be employed interchangeably.

For example, adding no polar solvent to glycerol would lead to about 8.2 percent salt in the final glycerol product. On the other hand, adding polar solvent to glycerol at a weight ratio of about 2.1 would lead to about 2 percent salt in the final glycerol product. Similarly, adding polar solvent to glycerol at a weight ratio of about 3.3 would lead to about 1 percent salt in the final glycerol product. Thus, the process can effectively tailor and fine-tune the final salt concentration in the glycerol end product (see Example 8, infra). The final yield of partially refined waste glycerol produced by this process usually ranges from about 97 percent to about 99 percent, depending on salt concentration.

Figure 4:
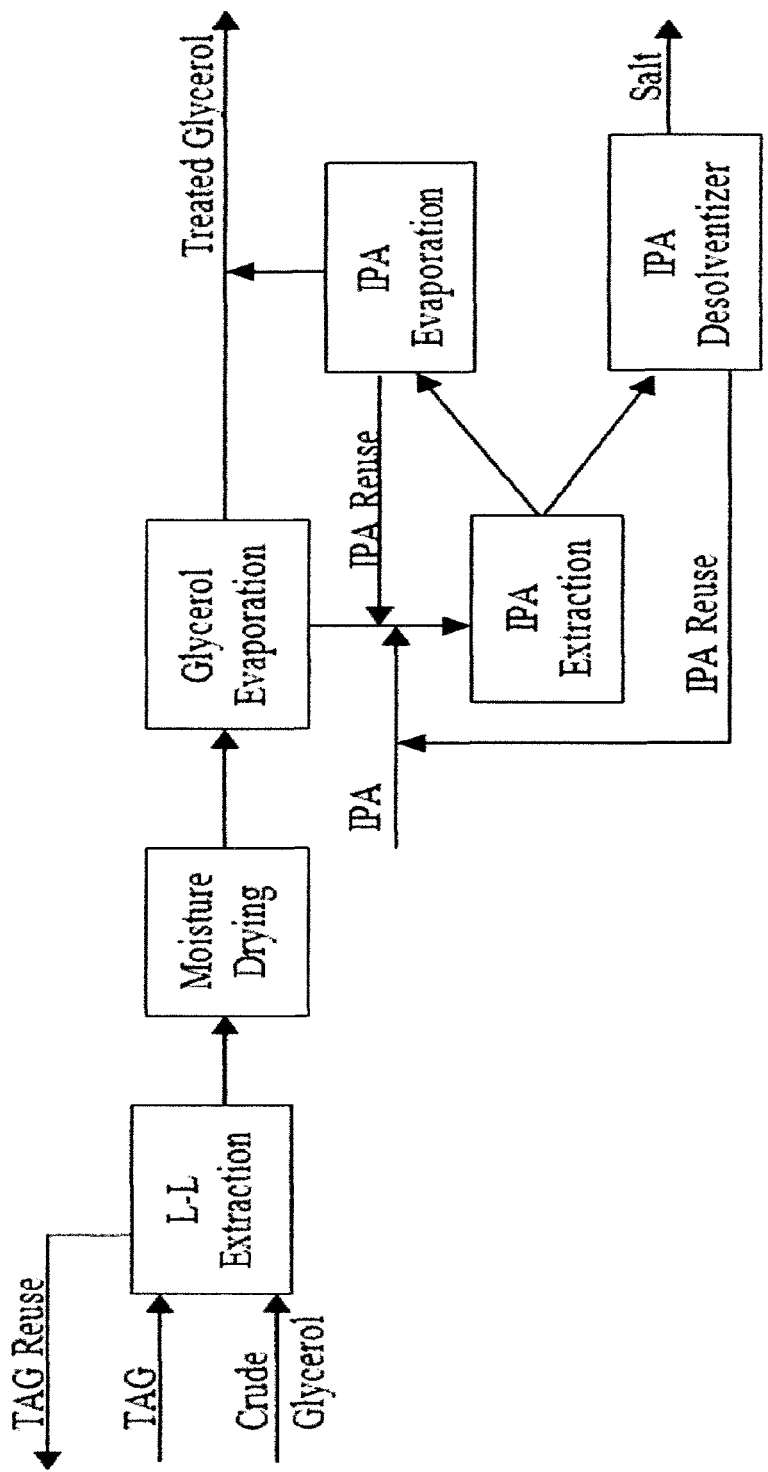
FIG. 4 is a block flow diagram showing another embodiment of the present disclosure. Herein.
Figure 5:
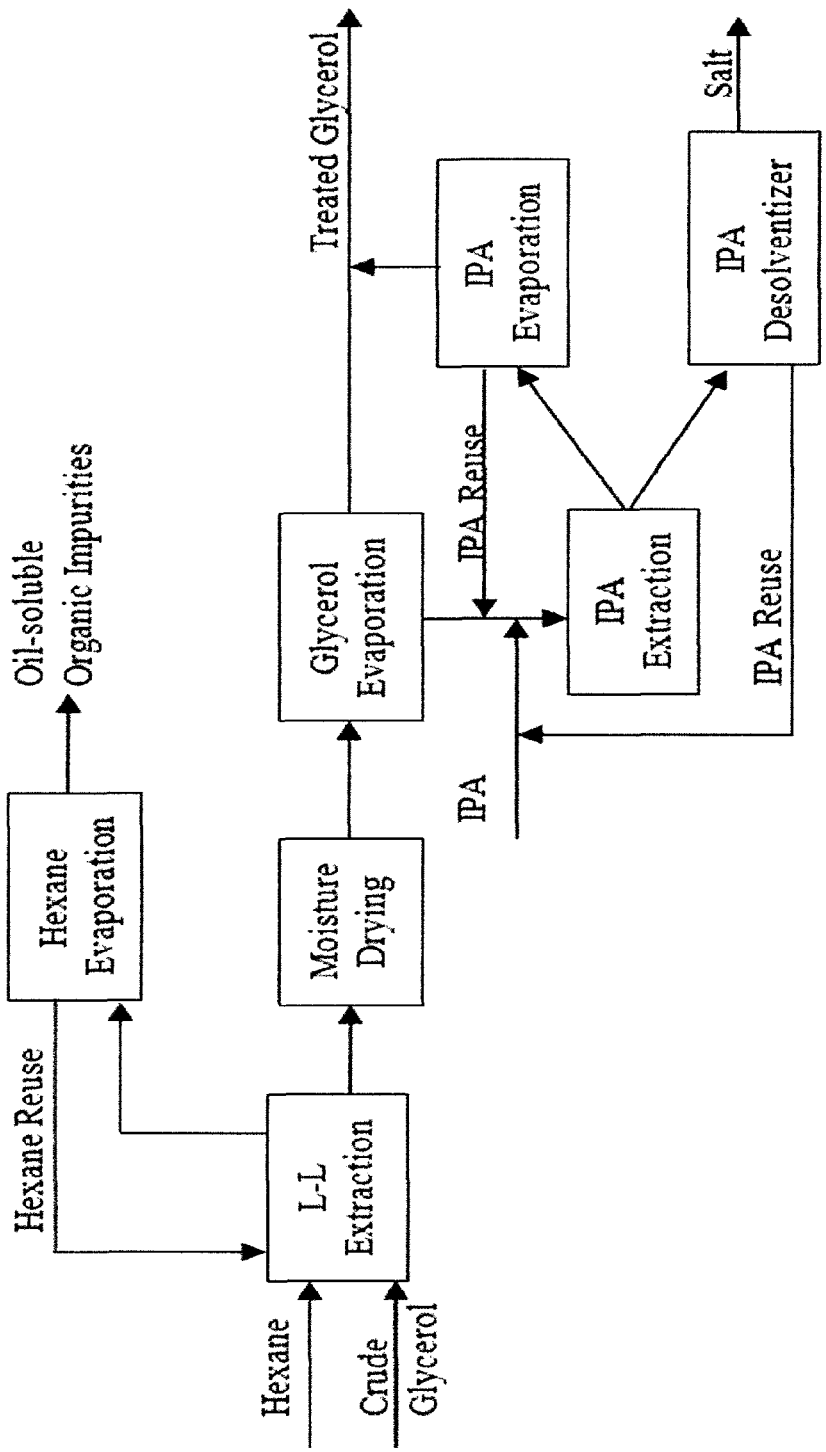
FIG. 5 is a block flow diagram showing another embodiment of the present disclosure. Herein.

The present disclosure provides a process for glycerol purification that further encompasses a hybrid process step for desalting glycerol (see FIGS. 4 and 5). For example, it is shown in FIGS. 4 and 5 that optional glycerol evaporation (i.e., partial glycerol evaporation) can lead to treated glycerol recovery without salt precipitation. This is accomplished by subjecting about 75 percent of glycerol (as a glycerol distillate) to partial evaporation, and then recovering the remaining approximately 25 percent glycerol in the evaporation discharge bottom, which is then further desalted by precipitating it via a polar solvent such as IPA. Thus, the system allows for clean glycerol to be recovered directly through partial evaporation leading to partially refined waste glycerol that is salt-free and between about 97 percent and about 99 percent pure. Herein, the partial glycerol evaporation produces about 75 percent clean and salt-free glycerol, while the rest of the remaining glycerol mixture is salt-saturated and subject to polar solvent (e.g., IPA) extraction. The clean glycerol derived from evaporation can be fed back into the system (or optionally used as a final product). Salt-saturating glycerol before IPA extraction allows the salt content of the final glycerol composition to be tailored and fine-tuned.

I. Deoiling Crude Glycerol

In various embodiments of the disclosure as shown in FIGS. 1 through 5, the crude glycerol is first subjected to a deoiling step for removal of the organic impurities. In other embodiments, however, the deoiling step may be performed after the dewatering step, or after the desalting step, or after the completion of the dewatering and desalting step. Deoiling may occur as either the first step, second step or final step in the process as shown in FIGS. 1A and 1B.

Crude glycerol contains about 80 percent to about 88 percent glycerol, about 6 percent to about 10 percent water, about 6 percent to about 8 percent salt (e.g., NaCl, KCl, $Na_2SO_4$, $K_2SO_4$), about 0.1 percent to about 3 percent organics and less than about 0.3 percent methanol. The organic oil-soluble impurities and contaminants that are contained within crude glycerol may include toxins that can inactive or pollute industrial processes that employ glycerol. Most of these contaminants are hydrophobic. The present method uses hydrophobic solvents such as, for example, hexane, TAG, butyl acetate, ethyl acetate, FAME, FAEE, fatty acid isopropyl ester, or the like to remove most of these organic contaminants from crude glycerol via solvent extraction. Some contaminants may have a more polar nature. For example, oxidized color bodies have polar characteristics in that they are not soluble in pure hexane but at least partially soluble in TAG, FAME, FAEE and fatty acid isoprophyl esters, and are highly soluble in butyl acetate and ethyl acetate. In one embodiment, a less expensive hexane is a hydrophobic solvent for deoiling crude glycerol containing medium to low levels of polar organic impurities. In another embodiment, butyl acetate or ethyl acetate is a hydrophobic solvent for deoiling crude glycerol containing higher levels of polar organic impurities.

In one embodiment, the hydrophobic solvent is nonvolatile and/or has a lower boiling point (bp) than oil-soluble organic impurities, has a low heat of vaporization ($\Delta Hv$) and has a low heat capacity (Cp). Examples of a hydrophobic solvent include, but are not limited to, TAG which has nonvolatile characteristics (see FIGS. 2 and 4); alkanes with $C_6$ to $C_{10}$ hydrocarbon chain-length or mixtures thereof (e.g., hexane; see FIGS. 3 and 5); alkenes with $C_6$ to $C_{10}$ hydrocarbon chain-length or mixtures thereof (e.g., hexene); and acetates such as, for example, ethyl acetate or butyl acetate, and fatty acid alcohol esters such as, for example, FAME, FAEE or fatty acid isopropyl esters. In one embodiment, the solvent is hydrophobic in nature. In another embodiment, the solvent is non-polar or polar in nature and is not miscible with water and glycerol. In another embodiment, the solvent has a lower boiling point and a lower heat of vaporization than water. In still another embodiment, the solvent has a higher boiling point than the oily organic impurities found in crude glycerol. In another embodiment, the solvent has a density that is lower than glycerol. The extraction efficiency of any of the hydrophobic solvents can be enhanced by the presence of about 6 percent to about 10 percent water in crude glycerol. Most oil-soluble impurities and contaminants presented in the crude glycerol are removed from the glycerol via solvent extraction regardless of the boiling points of the various contaminants.

Figure 2:
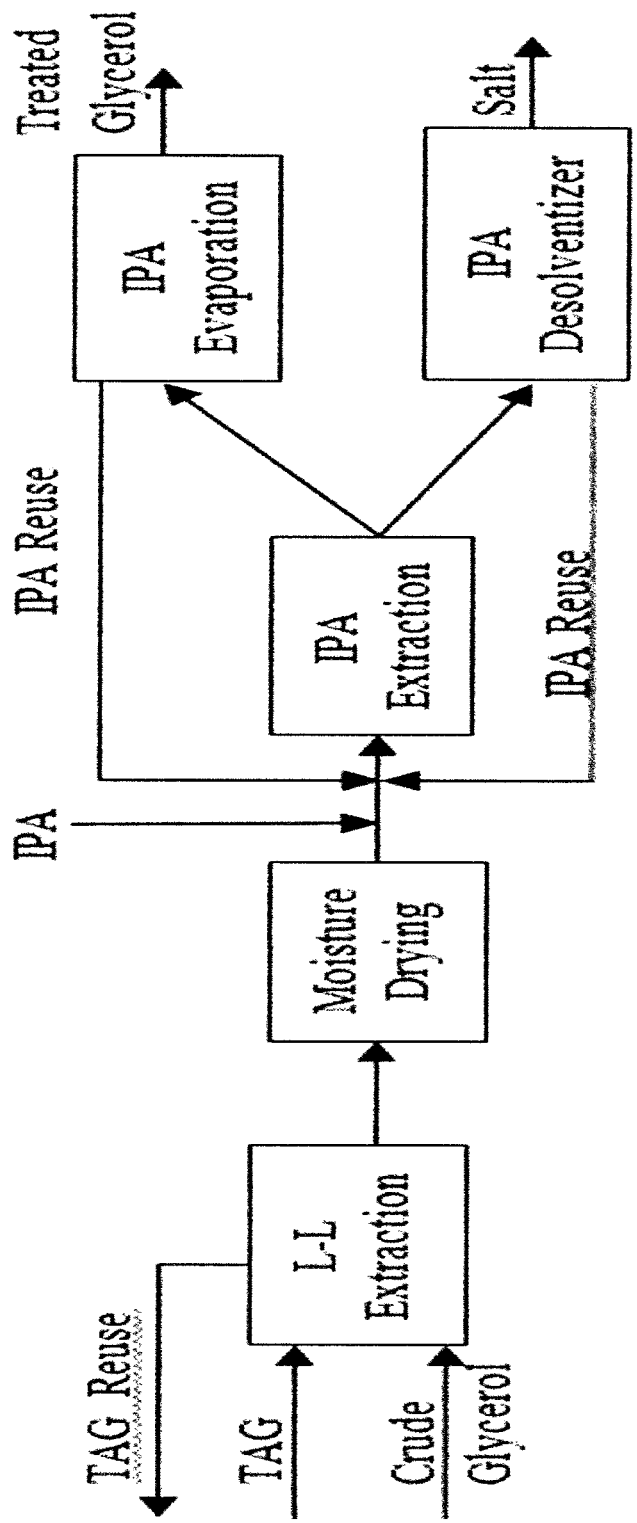
FIG. 2 is a block flow diagram showing one embodiment of the present disclosure. Herein.
Figure 3:
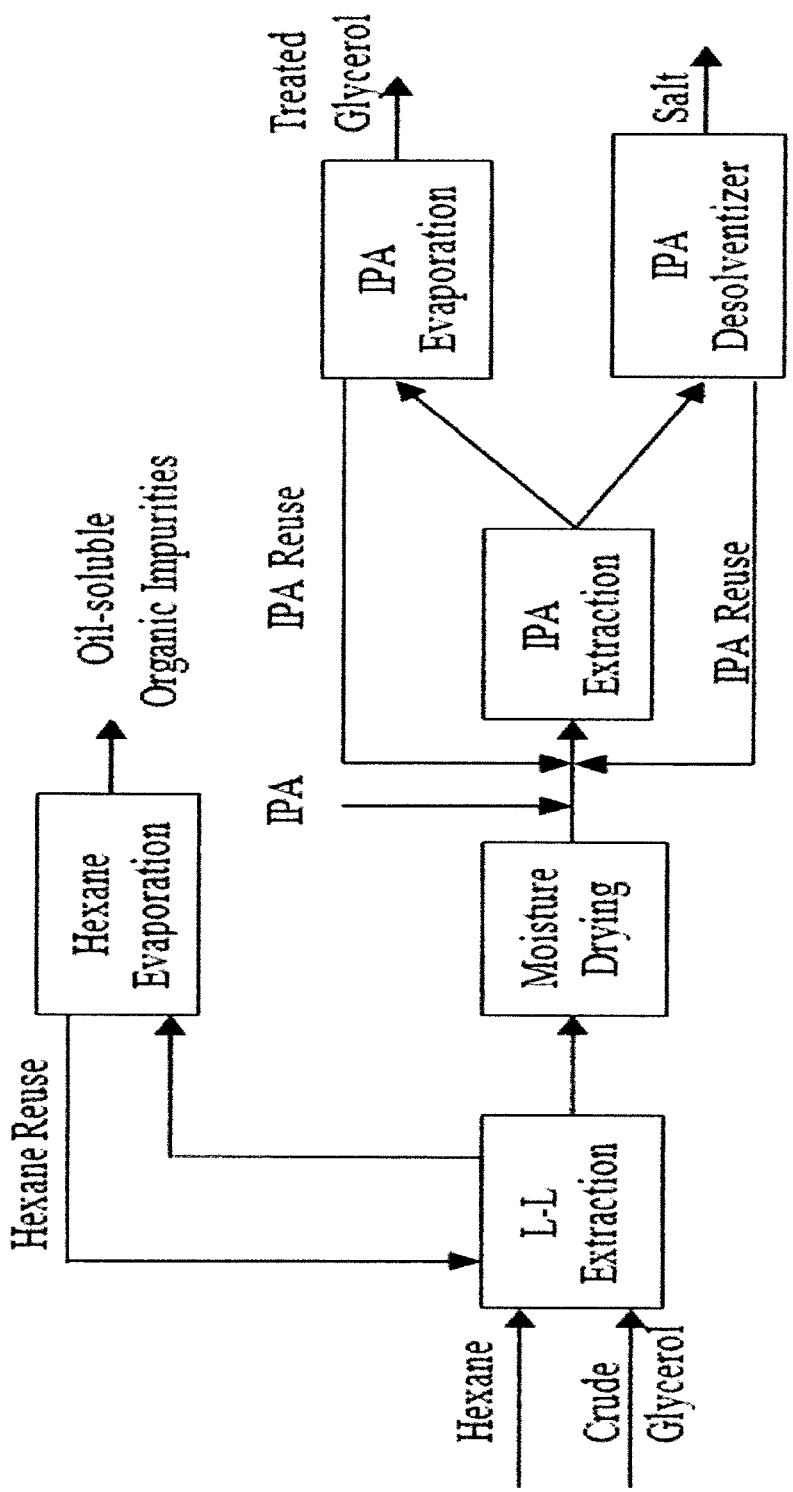
FIG. 3 is a block flow diagram showing another embodiment of the present disclosure. Herein.

One embodiment of the present disclosure is shown in FIG. 2 which provides a process for purifying crude glycerol wherein removal of oil-soluble impurities and contaminants is carried out via a hydrophobic solvent liquid-liquid extraction in order to produce deoiled (DO) glycerol. In one embodiment, partially refined waste glycerol encompasses DO glycerol. The amount of solvent used depends on the amount of oil-soluble impurities that are present in the crude glycerol. If deoiling is carried out in a biodiesel facility, TAG can be one of the solvents, because spent TAG can be re-used as biodiesel feed after the deoiling extraction has been completed (see FIGS. 2 and 4). The spent TAG contains TAG and extracted TAG soluble organic impurities. This generates fewer waste products during the glycerol purification process. In one embodiment, about 5 percent to about 20 percent of TAG (e.g., refined vegetable oil such as corn oil) can be used to prepare DO glycerol. In another embodiment, the solvent extraction can be carried out at about 20 to 95° C. In another embodiment, the solvent extraction can be carried out at about 20 to 95° C. and more preferably at about 40 to 80° C. from about 5 minutes to about 30 minutes under vigorous mixing. In another embodiment, the solvent extraction can be carried out at about 55 to 65° C. In another embodiment, the solvent extraction can be carried out at about 55 to 65° C. from about 5 minutes to about 30 minutes under vigorous mixing. In another embodiment, the solvent extraction can be carried out at about 60° C. In another embodiment, the solvent extraction can be carried out at about 60° C. from about 5 minutes to about 30 minutes under vigorous mixing. In another embodiment, solvent extraction is followed by gravity decantation, hydrocyclone separation, and/or low speed liquid-liquid centrifugal separation.

If deoiling is carried out at a facility remote from or unrelated to a biodiesel facility, or if the use of a differing solvent is desired for the purposes of increasing the purity of crude glycerol containing low levels of polar organic impurities, another hydrophobic solvent available for use is alkane. In one embodiment, the hydrophobic solvent is an acetate such as butyl acetate. In another embodiment as shown on FIG. 3, a useful hydrophobic solvent is hexane. Hexane has a boiling point of 69° C., 145 btu/lb heat of vaporization ($\Delta Hv$), and 0.53 btu/lb ° C. heat capacity (Cp). In one embodiment, about 5 percent to about 20 percent of hexane can be used to prepare DO glycerol. The amount of hexane required for extraction depends on the amount of oil-soluble impurities (e.g., polar and/or non-polar oil-soluble impurities) that are present in crude glycerol. Oil-soluble impurities that have been extracted can be removed through flash evaporation of the hydrophobic solvent as an evaporator bottom. For example, when about 5 percent hexane is used for deoiling crude glycerol, then recovery of hexane through flash evaporation requires about 22,000 btu/mt of crude glycerol. Along those same lines, when about 10 percent hexane is used for deoiling crude glycerol, then recovery of hexane through flash evaporation requires about 44,000 btu/mt of crude glycerol.

The density of hexane, vegetable oil and glycerol are 0.659 g/ml, 0.88 g/ml and 1.26 g/ml, respectively. When the hydrophobic solvent is combined with glycerol in order to remove the oil-soluble impurities and contaminants, the resulting mixture is separated into a DO glycerol phase and a hexane/contaminants phase by low g-force gravity separation. The hexane solvent is then recovered from a hexane/contaminant stream by flash evaporation. In one embodiment, a low g-force gravity separation is used to separate the hydrophobic solvent part containing oil-soluble organic impurities and contaminants from the crude glycerol part. Due to the larger density difference between the solvent part (that contains the impurities and contaminants) and the glycerol part, a low g-force is sufficient to effectively separate the two parts. In one embodiment, the density separation is carried out at about 10 to about 1000 g-force. In another embodiment, the density separation is carried out at about 25 g-force. In still another embodiment, the density separation is carried out at about 20 g-force (e.g., via a hydrocyclone). In some embodiments, a gravity decantation, a hydro-cyclone, and/or a low speed liquid-liquid centrifugal separator (e.g., CINC L-L separator) can be used for this type of separation. After the density separation, the hydrophobic solvent is recovered through flash evaporation. The recovered solvent is then recycled for reuse. The oil-soluble organic impurities and contaminants can be used as a boiler fuel. This step generates few to no waste products.

II. Dewatering Deoiled Glycerol

In various embodiments of the disclosure as shown in FIGS. 1 through 5, the dewatering step immediately follows the deoiling step. In other embodiments, however, the dewatering step may be performed as the initial step. Dewatering may occur as either the first step, second step or final step in the process as shown in FIGS. 1A and 1B.

The DO glycerol produced above (supra) may still contain some water. In one embodiment, it contains about 6 percent to about 10 percent water. DO glycerol can be dewatered through moisture drying (e.g., evaporation) in order to produce deoiled and dewatered (DOW) glycerol. In one embodiment, partially refined waste glycerol encompasses DOW glycerol. In another embodiment, DO glycerol is dewatered at about 60 to about 130° C. In another embodiment, DO glycerol is dewatered at about 90° C. and about 20 to about 60 torr resulting in less than about 0.5 percent moisture content. In one embodiment, DO glycerol is dewatered at about 90° C. and about 60 torr resulting in less than about 0.5 percent moisture content. In another embodiment, DO glycerol is dewatered at about 110° C. and about 60 torr resulting in less than about 0.5 percent moisture content. In still another embodiment, DO glycerol is dewatered at about 130° C. and about 60 torr resulting in less than about 0.5 percent moisture content. During dewatering of DO glycerol, shown as the moisture drying step in FIGS. 2 through 5, impurities that have a low boiling point as well as trace levels of methanol are removed. Any water evaporator can be used herein as equipment for moisture drying, wherein optimal moisture drying conditions are determined by following the manufacturer's suggestions (e.g., ASPEN modeling). The evaporated water is cooled and captured as condensate water. The condensate water contains methanol and small amount of hydrophobic solvent. The hydrophobic solvent, which is not miscible in water, is recovered by gravity decantation. The waste water containing methanol in the bottom layer of the decanter is about 6% to about 10% of crude glycerol.

III. Desalting Deoiled and Dewatered Glycerol

In various embodiments of the disclosure as shown in FIGS. 1 through 5, the desalting step is the final process operation performed in the production of the products—the partially refined waste glycerol or the fermentation grade glycerol. In other embodiments, however, the dewatering step may be performed as the initial step or following the initial step in the process. Desalting may occur as either the first step, second step or final step in the process as shown in FIGS. 1A and 1B.

The DOW glycerol produced above (supra) contains about 88 percent to about 91 percent glycerol, about 0.5 percent water, and about 7 percent to about 9 percent salt (e.g., NaCl) and trace amounts of organics. After deoiling and dewatering the crude glycerol, desalting of DOW glycerol can be carried out in two different ways that are interchangeable, including desalting of the DOW glycerol via a polar solvent (e.g., via alcohols such as IPA or butanol; or via phenols) (also shown in FIGS. 2 and 3); or optional partial evaporation of the DOW glycerol followed by desalting of the evaporation bottom via a polar solvent (e.g., via alcohols such as IPA or butanol; or via phenols) in order to produce deoiled, dewatered and desalted (DOWS) glycerol (shown in FIGS. 4 and 5). Thus, the second way contemplates a hybrid process step for desalting glycerol. In one embodiment, partially refined waste glycerol encompasses DOWS glycerol.

More specifically, the first way of desalting includes (1) polar solvent precipitation of salt from the DOW glycerol, (2) density separation of salt at a low g-force and (3) flash evaporation of the polar solvent from the polar solvent-glycerol mixture and from the solvent salt mixture. The second way of desalting includes (1) partial evaporation of the DOW glycerol, (2) polar solvent precipitation of the evaporation bottom, (3) density separation of salt at a low g-force and (4) flash evaporation of the polar solvent from the polar solvent-glycerol mixture and from the solvent salt mixture. The polar solvents that can be used are, for example, alcohols such as IPA or butanol, and phenols. FIGS. 4 and 5 provide block flow diagrams that show differing embodiments wherein the hybrid process step for desalting DOW glycerol is utilized.

In the first method as shown in FIGS. 2 and 3, the DOW glycerol is added to the polar solvent that acts as a solvent to precipitate super-saturated salt from the resulting polar solvent-glycerol mixture. This is carried out at a temperature that ranges from about 20 to about 100° C., and more particularly at a temperature that ranges from about 40 to about 80° C. In another embodiment, the temperature ranges from about 50 to about 70° C. In one embodiment, the DOW glycerol is added to the polar solvent that acts as a solvent to precipitate super-saturated salt from the resulting polar solvent-glycerol mixture at 60° C. In one another, the polar solvent is IPA. In another embodiment, the polar solvent is butanol. In yet another embodiment, the polar solvent is a phenol. In one embodiment, the density separation is carried out at about 10 to about 50 g-force. In another embodiment, the density separation is carried out at about 25 g-force. In still another embodiment, the density separation is carried out at about 20 g-force. In some embodiments, a gravity decantation, or a hydrocyclone can be used for this type of separation, with the light phase containing the glycerol and the heavy phase containing precipitated salt. In one embodiment, the polar solvent-glycerol solution saturated with salt (the light phase) is then flash evaporated at about 80° C. and about 60 torr to recover the polar solvent. In another embodiment, the polar solvent-glycerol solution saturated with salt is flash evaporated at about 90 to about 100° C. and at ambient pressure to recover the polar solvent.

Figure 1B:
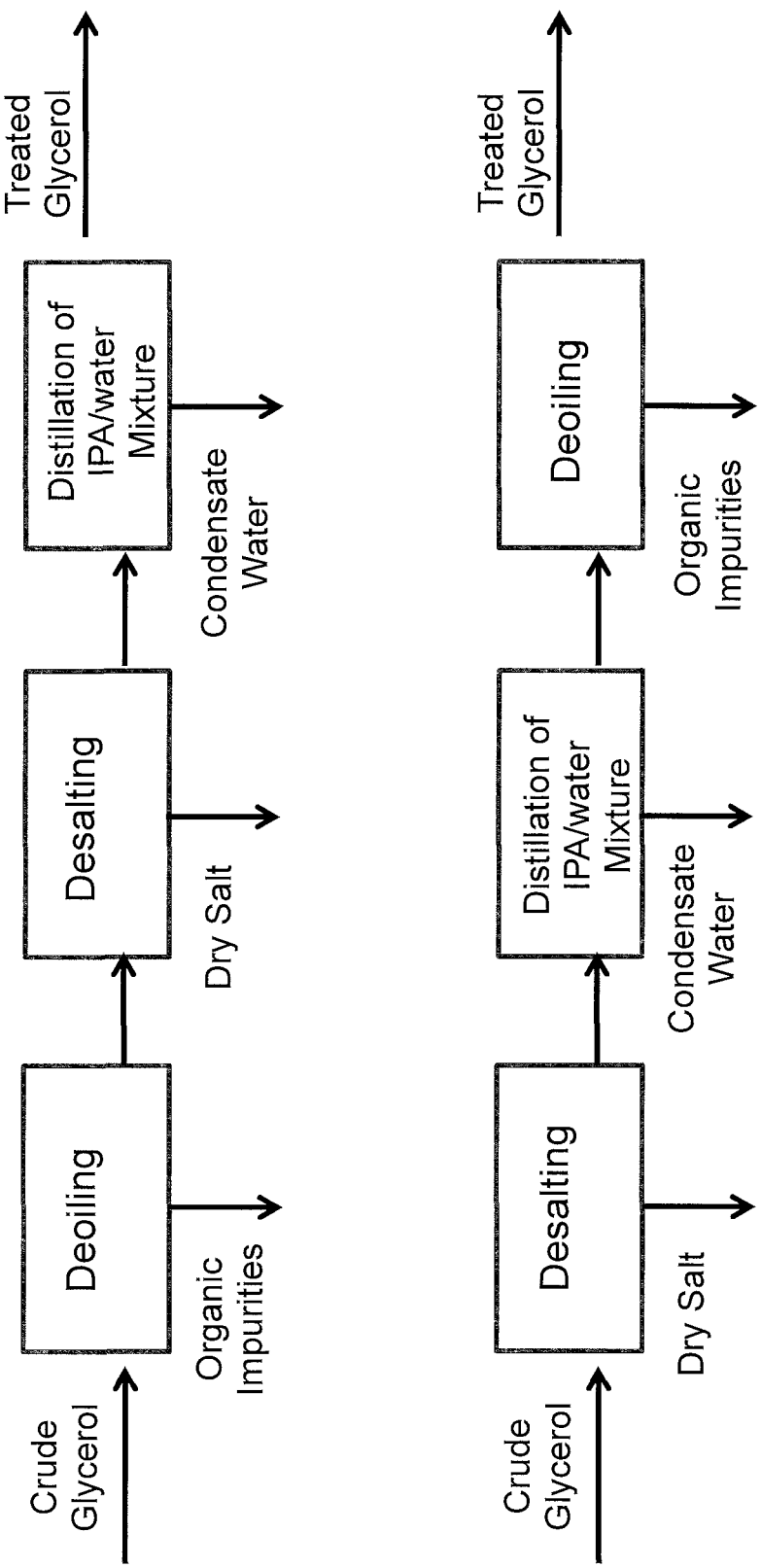

One embodiment involves the initial process steps of deoiling followed by desalting. Another embodiment involves the initial process steps of desalting and deoiling. In either of these embodiments, it is unnecessary to perform a separate dewatering step. This occurs as a result of the need to separate the polar solvent such as IPA which operates to precipitate the salt from the mixture. The process of separating the polar solvent from the mixture after salt precipitation utilizes heat at or above the boiling point of the polar solvent, for example 80° C., and altered pressure, for example, 60 torr, to effectively boil off the solvent. In sum, the effective temperature may be altered by the alteration of the pressure at which vaporization occurs. In those embodiments as shown in FIG. 1B, where the dewatering step is not performed prior to the desalting step, the process of solvent removal by distillation wherein heat is applied to vaporize the solvent which also operates to vaporize the water in the glycerol thereby effectively removing the water from the product stream. In order to reuse the solvent, however, an additional step is necessary to separate the water from the solvent stream recovered by condensing the mixture vaporized from the glycerol.

The resulting evaporator bottom phase is salt reduced DOW glycerol. As noted above, the salt reduced glycerol that is also deoiled and dewatered is referred to as DOWS glycerol (i.e., deoiled, dewatered/dried, and desalted glycerol). The salt content in DOWS glycerol depends on the ratio of polar solvent to glycerol (supra). Thus, the salt content of DOWS glycerol can be tailored and fine-tuned as needed.

In the second method as shown in FIGS. 4 and 5, the DOWS glycerol is produced by subjecting about 75 percent of the DOW glycerol (as a glycerol distillate) to evaporation, and then recovering the remaining approximately 25 percent glycerol in the evaporation discharge bottom (which is then further desalted by precipitating it via a polar solvent as shown in the first method, supra). This is a hybrid process and the evaporated glycerol is generally free of salt. The salt content in the polar-solvent-desalted glycerol composition can then be tailored by applying the appropriate ratio of glycerol to IPA in order to produce a partially refined waste glycerol or fermentation grade glycerol as an end product. The glycerol distillate is an evaporated material containing mostly glycerol, about 0.5 percent water, and some trace levels of organic materials.

The two interchangeable desalting steps (i.e., with or without partial glycerol evaporation) provide the basis for the two different processes. Both processes include (1) deoiling, (2) dewatering and (3) desalting steps in any order. Since residual oil soluble organic impurities end-up in the evaporation bottom after deoiling, any oil-soluble organic impurities that remain at the end of the two processes are the same. The loss of glycerol yield employing any of the two interchangeable desalting steps is less than 1%. The loss of yield is low because any residual glycerol that is left with the polar solvent, which is contained in the salt matrix after polar solvent precipitation, can be further recovered by a polar solvent wash. Any residual polar solvent in the salt phase can be recovered through de-solventization and reused. This step generates few to no waste products.

The desalting step or salt removal can be used to collect the removed salt as a useful by-product which is nearly free from organic impurities and glycerol. The removed salt can be re-used in other processes. For example, the salt can be collected for use in industrial processes or for the use of industrial products. As such, various salts are contemplated herein including NaCl, KCl, $Na_2SO_4$, $K_2SO_4$, and others (see, e.g., Table 1B below). In one embodiment, NaCl is collected for use in animal nutrition, water softening, de-icing, and others. In another embodiment, KCl or $K_2SO_4$ is collected for use as agricultural fertilizer.

TABLE 1B

Examples of Salt Produced as By-Product after De-salting

| Homogeneous Base Catalyst | Neutralizing Acids | Salts |
| --- | --- | --- |
| sodium oxide ($Na_2O$), | hydrochloric acid (HCl), | Sodium chloride (NaCl), |
| sodium hydroxide (NaOH), | sulfuric acid ($H_2SO_4$), | sodium sulfate ($Na_2SO_4$), |
| sodium methoxide ($NaOCH_3$), | phosphoric acid ($H_3PO_4$), | sodium phosphate ($Na_3PO_4$), |
| sodium ethoxide ($NaOC_2CH_5$) | nitric acid ($HNO_3$) | sodium nitrate ($NaNO_3$) |
| | acetic acid ($C_2H_4O_2$), | sodium acetate ($C_2H_3NaO_2$), |
| | carbonic acid ($H_2CO_3$), | sodium carbonate ($Na_2CO_3$), |
| | formic acid ($CH_2O_2$), | sodium formate (HCOONa), |
| | lactic acid ($C_3H_6O_3$), | sodium lactate ($C_3H_5NaO_3$), |
| | gluconic acid ($C_6H_{12}O_7$), | sodium gluconate ($C_6H_{11}NaO_7$), |
| | citric acid ($C_6H_8O_7$), | sodium citrate ($C_6H_5Na_3O_7$), |
| | methanesulfonic acid ($CH_4O_3S$) | sodium methanesulfonate ($CH_3NaO_3S$) |
| | boric acid ($H_3BO_3$) | sodium borate ($Na_2B_4O_7$) |
| potassium oxide ($K_2O$), | hydrochloric acid (HCl), | potassium chloride (KCl), |
| potassium hydroxide (KOH), | sulfuric acid ($H_2SO_4$), | potassium sulfate ($K_2SO_4$), |
| potassium methoxide ($KOCH_3$), | phosphoric acid ($H_3PO_4$), | potassium phosphate ($K_3PO_4$), |
| potassium ethoxide ($KOC_2CH_5$) | nitric acid ($HNO_3$) | potassium nitrate ($KNO_3$) |
| | acetic acid ($C_2H_4O_2$), | potassium acetate ($CH_3CO_2K$), |
| | carbonic acid ($H_2CO_3$), | potassium carbonate ($K_2CO_3$), |
| | formic acid ($CH_2O_2$), | potassium formate ($CHKO_2$), |
| | lactic acid ($C_3H_6O_3$), | potassium lactate ($C_3H_5KO_3$), |
| | gluconic acid ($C_6H_{12}O_7$), | potassium gluconate ($C_6H_{11}KO_7$), |
| | citric acid ($C_6H_8O_7$), | potassium citrate ($C_6H_5K_3O_7$), |
| | methanesulfonic acid ($CH_4O_3S$) | potassium methanesulfonate ($CH_3KO_3S$) |
| | boric acid ($H_3BO_3$) | potassium borate ($K_2B_4O_7$) |

TABLE 1B-continued

Examples of Salt Produced as By-Product after De-salting

| Homogeneous Base Catalyst | Neutralizing Acids | Salts |
|---|---|---|
| guanidine (CH$_5$N$_3$) | hydrochloric acid (HCl), sulfuric acid (H$_2$SO$_4$), phosphoric acid (H$_3$PO$_4$), acetic acid (C$_2$H$_4$O$_2$), carbonic acid (H$_2$CO$_3$), citric acid (C$_6$H$_8$O$_7$), methanesulfonic acid (CH$_4$O$_3$S) | guanidine hydrochloride (CH$_5$N$_3$•HCl), guanidine sulfate (2(CH$_5$N$_3$)•H$_2$SO$_4$), guanidine phosphate (2(CH$_5$N$_3$)•H$_3$PO$_4$), guanidine acetate (CH$_5$N$_3$•C$_2$H$_4$O$_2$), guanidine carbonate (CH$_5$N$_3$•H$_2$CO$_3$), guanidine citrate (CH$_5$N$_3$•C$_6$H$_8$O$_7$), guanidine methanesulfonate (CH$_5$N$_3$•CH$_4$O$_3$S) |

Uses of Partially Refined Waste Glycerol

The present disclosure provides partially refined waste glycerol, including salt-containing partially refined waste glycerol that can be employed in industrial applications. The salt content of the partially refined waste glycerol can be tailored to various uses. In one embodiment, a partially refined waste glycerol with no salt content can be used in various industrial applications. In another embodiment, a partially refined waste glycerol with a specific salt content in the range from about 0.05 percent to about 8.2 percent can be used in various industrial applications. In another embodiment, a partially refined waste glycerol with a specific salt content in the range from about 0.05 percent to about 3.5 percent can be used as fermentation grade glycerol in fermentations that employ microbial hosts with a higher salt tolerance (e.g., marine organisms). In another embodiment, a partially refined waste glycerol with a specific salt content in the range from about 0.05 percent to about 2 percent can be used as fermentation grade glycerol in fermentations that employ microbial hosts with a lower salt tolerance (e.g., E. coli). In yet another embodiment, a partially refined waste glycerol with a specific salt content in the range from about 0.05 percent to less than about 8.2 percent can be used as fermentation grade glycerol in fermentations that employ microbial hosts with a higher salt tolerance. In yet another embodiment, a partially refined waste glycerol with a specific salt content in the range from about 0.05 percent to less than about 8.2 percent can be used as fermentation grade glycerol in fermentations that employ microbial hosts (e.g., E. coli) that have been altered such that they can tolerate a higher salt concentration than their native counterparts.

In another embodiment, partially refined waste glycerol can be used as a humectant, emulsifier and plasticizer and it is compatible with a wide variety of materials and mixes. In another embodiment, partially refined waste glycerol can be used as an adhesive such as with plasticizing and penetrating properties. In another embodiment, partially refined waste glycerol can be used for agriculture such as for sprays, dips and washes. In another embodiment, partially refined waste glycerol can be used as green antifreeze or automobile coolant. In another embodiment, partially refined waste glycerol can be used as a cleaner or polisher such as in the home, office and automobile market. In another embodiment, partially refined waste glycerol can be used to treat or alter materials such as leather (e.g., tanning and finishing) and textiles (e.g., facilitating printing and dying; lubricating and snag-proofing; antistatic-, antishrink-, and anticrease treatments; water-proofing; flame-proofing). In another embodiment, partially refined waste glycerol is used to process metals such as pickling, quenching, stripping, electroplating, galvanizing, and soldering. In still another embodiment, partially refined waste glycerol can be used to treat paper such as acting as a humectant, plasticizer, softening agent, and barrier agent (e.g., against grease and solvents). In another embodiment, partially refined waste glycerol can be used in photography as wetting and plasticizing agent. In another embodiment, partially refined waste glycerol can be used as resin, including ester gums, polyurethanes, and epoxies. In yet another embodiment, partially refined waste glycerol can be used in detergents.

EXAMPLES

The following examples further illustrate the disclosure but should not be construed in any way as limiting its scope.

In order to utilize crude glycerol that is derived from biodiesel production and other fat-splitting processes, it must be cost-effectively deoiled, dewatered and desalted in order to produce partially refined waste glycerol that is suitable for many industrial applications. The examples below describe the process that was developed in order to produce partially refined waste glycerol. The examples also show how salt-containing glycerol was made.

Example 1

Process of Producing Deoiled (DO) Glycerol using Vegetable Oil as Hydrophobic Solvent Crude glycerol (see Table 2, infra) was deoiled through a liquid-liquid extraction of oil-soluble impurities using triacylglycerides (TAG) as solvent. Vegetable oil (corn oil) was tested as the hydrophobic solvent since it is abundant at many biodiesel facilities. This separation was based on the large density difference between the hydrophobic solvent (0.88 g/ml for corn oil) and glycerol (1.26 g/ml) at a reduced glycerol viscosity (81.3 cp at 60° C.). Corn oil was combined with the crude glycerol (5:95 vol/vol) in a tank mixer, and thoroughly mixed at 60° C. for 5 minutes. The resulting crude glycerol-corn-oil mixture was separated into an oil phase and a deoiled glycerol phase by centrifugation at 20 g-force with a bucket centrifuge for 5 minutes at 40° C. This g-force was chosen because it is similar to what can be achieved by a hydro-cyclone. A low speed liquid-liquid centrifugal separator (CINC L-L) having about 1000 g-force may provide a similar or effective separation. As shown in Table 2 below, the organic impurities were significantly reduced in the resulting DO glycerol (from 394 ppm to 192 ppm).

TABLE 2

Characteristics of Glycerol Stages While Comparing
Crude Glycerol to Partially Refined Waste Glycerol
(DO-, DOW-, DOWS Glycerol)

| | Unit | Crude Glycerol | DO Glycerol | DOW Glycerol | DOWS-2 Glycerol |
|---|---|---|---|---|---|
| Glycerol Refining Process | | None | Deoiled | Deoiled and Dried | Deoiled, Dried and Desalted |
| Glycerol Content | % | 81.99 | 82.0 | 92.66 | 97.94 |
| NaCl | % | 6.42 | 6.42 | 7.25 | 2.0 |
| Water | % | 11.56 | 11.56 | 0.07 | 0.12 |
| Organic Impurities | ppm | 342 | 192 | 222 | 222 |

Example 2

Process of Producing Deoiled (DO) Glycerol using Hexane as Hydrophobic Solvent

Hexane can be used as an alternative hydrophobic solvent for deoiling of crude glycerol as shown in Example 1. Hexane has a boiling point of 69° C., 145 btu/lb heat of vaporization ($\Delta Hv$), and 0.53 btu/lb° C. heat capacity (Cp). Deoiling is achieved via hydrophobic solvent liquid-liquid extraction using a low volume of hexane and a flash evaporator unit. Hexane is thoroughly mixed with the crude glycerol at 5:95-20:80 (vol/vol) at ambient temperature for 5-30 minutes. The resulting mixture is then separated into an organic light phase and a glycerol heavy phase using a hydro-cyclone or a low-speed liquid-liquid centrifugal separator. Hexane is recovered from the extracted organic impurities by flash evaporation and recycled. The evaporator bottoms containing the organic impurities can be used as fuel for value recovery and reduction of waste. The DO glycerol is expected to have a decrease in organic impurities similar to or better than that achieved using vegetable oil.

Example 3

Process of Producing Deoiled and Dewatered (DOW) Glycerol by Dewatering DO Glycerol DO glycerol (from Example 1) contained about 12% water. In order to remove this water, a moisture drying process was carried out at 100° C. and 60 torr, using a lab scale glass evaporator. A shown in Table 2 (supra), the resulting deoiled and dewatered (DOW) glycerol contained less than 0.5% moisture content (water). While not determined, trace levels of methanol and low boiling point species are expected to be reduced along with water from the glycerol during the dewatering process. The DOW glycerol still contained about 7.25% salt.

Example 4

Process of Producing Deoiled, Dewatered and Desalted (DOWS) Glycerol by Desalting DOW Glycerol Via IPA Precipitation As shown in Table 2 (supra), DOW glycerol contained 7.25% NaCl. In order to decrease the concentration of NaCl, desalting was carried out by isopropanol (IPA) precipitation and density separation. IPA was thoroughly mixed with DOW glycerol in a mixing tank at 3.2:1 IPA:DOW glycerol (wt/wt) at 60° C. for 30 minutes, and the resulting super salt saturated mixture was agglomerated for 30 minutes at 60° C. This temperature (60° C.) was selected because it permitted almost complete salt precipitation at a temperature 22.3° C. below the boiling point of IPA while supporting a favorable viscosity of the resulting mixture for rapid settling of crystallized NaCl, including fine crystals. The solids were then removed by density separation, using a bucket centrifuge at 20 g-force for 5 minutes at 40° C. The liquid glycerol-IPA mixture was decanted, and the IPA was removed by evaporation at 80° C. and 60 torr. As shown in Table 2 (supra), the resulting deoiled, dewatered, and desalted (DOWS) glycerol contained significantly less NaCl (1.94%) than DOW glycerol (7.25%). The sample in Table 2 is referred to as DOWS—2 glycerol (i.e., glycerol containing about 2% salt), where the 1.94 refers to the concentration (wt/wt) of NaCl in the DOWS glycerol.

Example 5

Process of Producing Deoiled, Dewatered and Desalted (DOWS) Glycerol by Desalting DOW Glycerol Via IPA Precipitation and Partial Glycerol Evaporation An alternative way of decreasing the salt concentration of DOW glycerol by IPA precipitation is to evaporate a majority of the glycerol in DOW glycerol, and then remove the salt remaining in the evaporation bottom by IPA precipitation as shown in Example 4. In this way a smaller volume of IPA needs to be used in the precipitation, a salt free glycerol can be recovered through evaporation, and the salt content of the final partially refined waste glycerol can be adjusted by appropriate blending of evaporated glycerol with IPA precipitated DOW glycerol. DOW glycerol was first treated at 152.3° C. vapor temperature at 5 torr until 75% of the glycerol had evaporated. As shown in Table 3 below the evaporated glycerol (DOWS—0 glycerol) (i.e., DOWS glycerol containing about 0% salt) was significantly purified and contained only 0.023% NaCl. The super salt saturated glycerol evaporation bottom was thoroughly mixed with IPA at 5.7:1 IPA:DOW glycerol evaporation bottom (wt/wt) in a mixing tank at 60° C. for 5 minutes, and the resulting mixture was agglomerated for 30 minutes at 60° C. The solids were removed by density separation in a bucket centrifuge by applying 20 g-force for 5 minutes at 40° C. The liquid IPA glycerol supernatant was decanted, and the IPA was recovered by flash evaporation (supra). As shown in Table 3 below (infra), the resulting glycerol in the evaporation bottom contained 0.97% (wt/wt) NaCl, and this sample is referred to as DOWS—1 glycerol (i.e., DOWS glycerol containing about 1% salt).

TABLE 3

Fatty Acid Methyl Ester (FAME) Production with DOWS Glycerol Compositions as Feedstock

|  | Units | USP Grade | DOWS-0 | DOWS-0.1 | DOWS-0.5 | DOWS-1 |
|---|---|---|---|---|---|---|
| Glycerol Feed | | | | | | |
| Glycerol Content | % | 99.5 | 99.5 | 99.7 | 99.2 | 98.8 |
| NaCl | % | N/A | 0.023 | 0.1 | 0.5 | 0.97 |
| Organics | ppm | N/A | 60 | 110 | 240 | 639 |
| Water | % | 0.5 | 0.46 | 0.21 | 0.29 | 0.15 |
| Methanol | % | N/A | N/A | N/A | N/A | N/A |
| Fermentation | | | | | | |
| Fermentation Yield | % | 24.2 | 20.4 | 22.5 | 22.2 | 26.5 |
| Fermentation Productivity | g/l/hr | 1.33 | 1.08 | 1.20 | 1.16 | 1.45 |
| Fermentation Titer | g/kg | 95.4 | 77.2 | 86.2 | 83.4 | 103.9 |
| Harvest | | | | | | |
| Centrifugation Yield Crude FAME | % | 54.2 | 43.2 | 69.2 | 60.3 | 87.0 |
| Acid No. | mg KOH/g | 3.49 | 4.63 | 4.46 | 4.18 | 3.23 |
| Carbonyl | ppm | 3026 | 2794 | 2079 | 2377 | 2239 |
| Moisture | % | 2.23 | 2.01 | 2.23 | 2.43 | 1.63 |

Example 6

Process of Desalting Crude Glycerol

In order to evaluate the quality of desalted crude glycerol that was not deoiled, crude glycerol was directly desalted by IPA precipitation as shown in Example 3. As shown in Table 4 below the resulting desalted (DS) glycerol contained 2% (wt/wt) NaCl (see DS-2).

TABLE 4

Fermentation Comparison for FAME Production

|  | Unit | USP Glycerol | Crude Glycerol | DO glycerol | DS-2 | DOWS-2 |
|---|---|---|---|---|---|---|
| Glycerol Feed | | | | | | |
| Glycerol | % | 99.5 | 82.0 | 92.66 | 96.97 | 97.92 |
| Oil-Soluble Organics | ppm | 0 | 533 | 191 | 570 | 222 |
| Salt (NaCl) | % | 0 | 6.4 | 7.25 | 2.0 | 2.0 |
| Water | % | 0.5 | 11.56 | 0.07 | 1.03 | 0.12 |
| Fermentation | | | | | | |
| Fermentation Time | hr | 72 | 48 | 72 | 72 | 72 |
| Yield | % | 21.9 | 16.4 | 19.8 | 19.2 | 19.5 |
| Productivity | g/l/hr | 1.158 | 0.478 | 0.519 | 0.873 | 0.938 |
| Titer | g/kg | 83.7 | 35.9 | 44.0 | 62.9 | 67.5 |

Example 7

Figure 6:
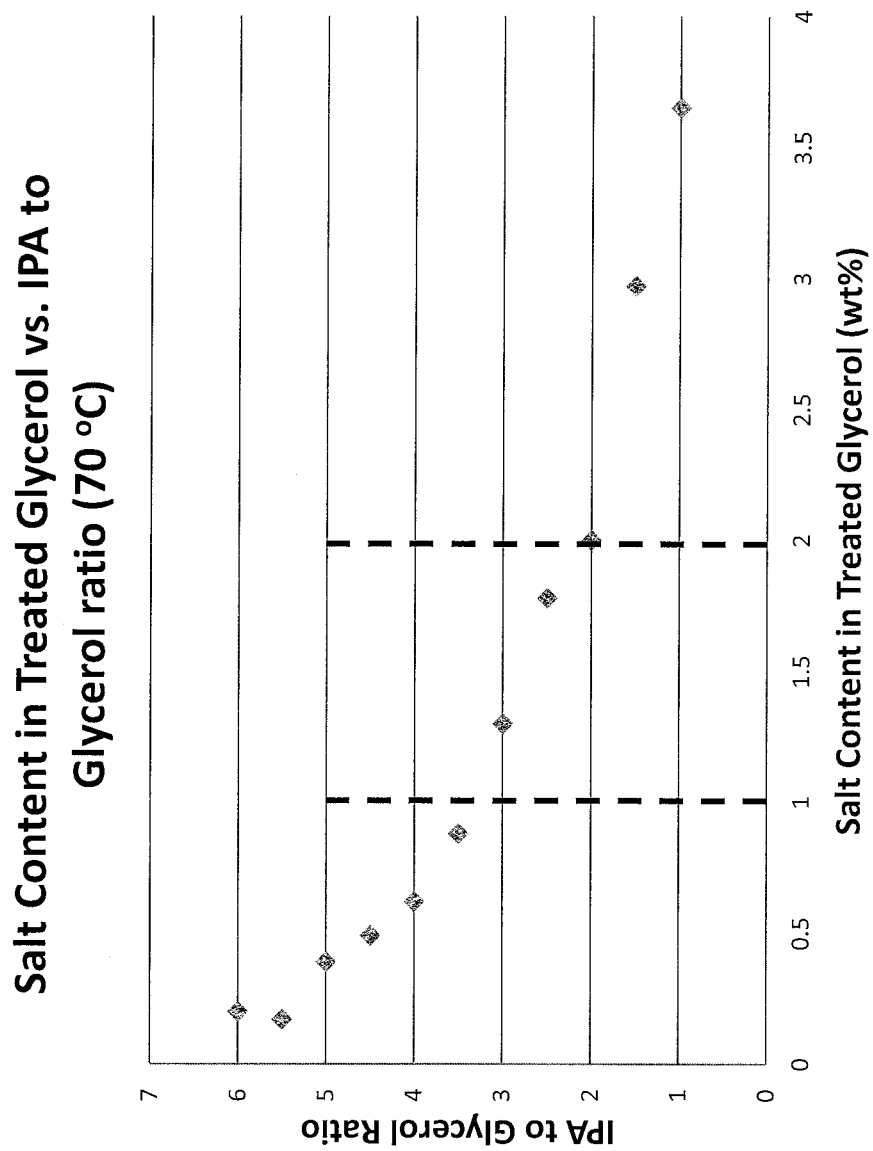
FIG. 6 is a graph showing another embodiment of the present disclosure. Herein.

Process for the Preparation of a DOWS Composition that was Salt-Tailored with NaCl by Blending Different Refined Glycerol Samples Since different applications for partially refined waste glycerol exist, glycerol can benefit from having different salt concentrations. Various DOWS glycerol compositions with a NaCl content ranging from 0 to 7.25% were made. These compositions were prepared by controlling the ratio of the IPA to glycerol in the IPA precipitation step. IPA was thoroughly mixed with DOW glycerol at varying ratios, and the samples were processed as described in Example 3 (supra). As shown in FIG. 6, at lower ratios, higher salt concentrations result, while at higher ratios lower salt concentrations result.

Example 8

Process for the Preparation of a DOWS Composition that was Salt-Tailored with NaCl by Controlling the Ratio of IPA to Glycerol in the IPA Precipitation Process Since different applications of partially refined waste glycerol may benefit from different salt concentrations in the glycerol, DOWS glycerol compositions containing NaCl ranging from 0 to 1% were prepared by blending the evaporated glycerol (DOWS—0) with DOWS—1. Various samples were prepared by using this method as shown in Table 5 (infra).

TABLE 5

Examples of Salt-Tailored Glycerol Compositions

|  | DOWS-0 No Salt | DOWS-0.1 0.1% Salt | DOWS-0.5 0.5% Salt | DOWS-1 1.0% Salt |
|---|---|---|---|---|
| NaCl % in DOWS Glycerol | 0.023% | 0.1% | 0.5% | 0.97 |
| Blend Ratio (DOWS No Salt:DOWS 1.0% Salt) | 1:0 | 9:1 | 1:1 | 0:1 |

Example 9

Testing Various Forms of Glycerol in a Fame Fermentation

This example compares the use of crude glycerol, DO glycerol, DS-2 glycerol (desalted to 2% salt), DOWS—2 glycerol (containing about 2% salt), and USP glycerol, as the sole carbon source in fermentation using an organism that does not tolerate crude glycerol well. As a representative example, the fermentation chosen was one to produce fatty acid methyl esters (FAME) using an engineered *E. coli* biocatalyst. Each sample was prepared as described above, and the specifications of each glycerol sample and how they performed as a carbon source in fermentations are shown in Table 4 (supra). These data demonstrate that partial refining of crude glycerol using the methods described herein significantly improve its ability to support efficient fermentation. In particular both the decrease in organic and salt impurities increase fermentation performance in comparison to crude glycerol.

Example 10

Testing Salt-Tailored DOWS Glycerol Compositions in a Fame Fermentation

This example investigates the feasibility of salt-tailored DOWS glycerol in fermentations, wherein the DOWS glycerol compositions contain a specifically tailored salt content and reduced oil-soluble organic impurities. DOWS 0, 0.1, 0.5, and −1 glycerol were made from crude glycerol as described above and in Example 8 and shown in Table 5.

In the fermentation evaluation, the DOWS glycerol samples supported comparable FAME yield, productivity and titer (YPT) and produced similar quality of FAME product as compared to USP grade glycerol. However, as shown in Table 3 (supra), DOWS—1 surprisingly outperformed the USP glycerol in these fermentations. These data suggest that partially refined glycerol is superior to USP glycerol as a fermentation feedstock and that salt tailored DOWS is a useful tool for the production of high performance fermentation feedstocks from waste glycerol. Indeed, these data demonstrate that the salt impurities in waste glycerol that traditionally are considered an inhibitor to fermentation can be leveraged to improve fermentation.

Example 11

Evaluation of the Impact of Salt Tailored DOWS on the Recovery of FAME from Fermentation Broths Impurities in feedstocks can influence the efficiency of product recovery from fermentation broths. In order to evaluate the impact of different DOWS of tailored salt concentration on FAME recovery from fermentation broths, oil was recovered from each fermentation described in Example 10. The broth from each of the fermentation described in Table 3 (supra) was gravity separated using a bucket centrifuge at 5000 g-force for 15 minutes at 40° C., and the light oil phase containing the FAME from each sample was recovered by decantation. The efficiency of FAME recovery from the broth is reported as the percent of FAME recovered as compared to the total FAME in the broth before centrifugation. As shown in Table 3 (supra), recovery was most efficient from the fermentation broth of DOWS—1 followed by those that had salt. Recovery was least efficient from USP and DOWS—0. This data suggests that tailoring the level of impurities remaining in partially refined waste glycerol can provide a benefit on fermentation and product recovery processes and that DOWS—1 is a good fermentation feedstock.

As is apparent to one with skill in the art, various modifications and variations of the above aspects and embodiments can be made without departing from the spirit and scope of this disclosure. Such modifications and variations are within the scope of this disclosure.

We claim:

1. A process of producing partially refined waste glycerol by refining crude glycerol containing organic impurities, said process comprising:
    deoiling using a hydrophobic solvent to extract organic impurities;
    dewatering by drying at an elevated temperature; and
    desalting using a polar solvent to precipitate salt.

2. A process of producing partially refined waste glycerol by refining crude glycerol containing organic impurities, said process comprising:
    subjecting crude glycerol to a hydrophobic solvent to produce a mixture of crude glycerol and hydrophobic solvent; and
    separating the mixture of crude glycerol and hydrophobic solvent to produce a deoiled (DO) glycerol and a phase containing hydrophobic solvent and organic impurities.

3. The process of claim 2, further comprising the step of drying said DO glycerol to produce a deoiled and dewatered (DOW) glycerol.

4. The process of claim 3, further comprising the steps of:
    subjecting a polar solvent to said DOW glycerol to produce a mixture of polar solvent and DOW glycerol and precipitating a salt from the mixture of polar solvent and DOW glycerol; and
    separating the mixture of polar solvent and DOW glycerol into a light phase containing a deoiled, dewatered and desalted (DOWS) glycerol and the polar solvent and a heavy phase containing the salt.

5. The process of claim 4, further comprising the step of removing the polar solvent from the light phase to produce a purified DOWS glycerol.

6. The process of claim 4, further comprising the step of partially evaporating the DOW glycerol before subjecting it to the polar solvent.

7. The process of claim 2, further comprising the steps of:
    subjecting a polar solvent to said DO glycerol to produce a mixture of polar solvent and DO glycerol and precipitating a salt from the mixture of polar solvent and DO glycerol; and
    separating the mixture of polar solvent and DO glycerol into a light phase containing a deoiled and desalted glycerol and the polar solvent and a heavy phase containing the salt.

8. The process of claim 7, further comprising the step of drying said deoiled and desalted glycerol to produce a deoiled, desalted and dewatered (DOWS) glycerol.

9. The process of claim 5, wherein said DOWS glycerol is a fermentation grade glycerol.

10. The process of claim 2, wherein said hydrophobic solvent is selected from the group consisting of triacylglyceride, alkane, alkene, acetate, and fatty acid alcohol ester.

11. The process of claim 10, wherein said triacylglyceride is vegetable oil.

12. The process of claim 10, wherein said acetate is butyl acetate.

13. The process of claim 10, wherein said alkane is hexane.

14. The process of claim 2, wherein said organic impurities are oil-soluble.

15. The process of claim 2, wherein said DO glycerol comprises less than about 195 ppm oil-soluble organic impurities.

16. The process of claim 3, wherein said DOW glycerol comprises less than about 0.5 percent water.

17. The process of claim 4, wherein said polar solvent is an alcohol.

18. The process of claim 17, wherein said alcohol is isopropanol or butanol.

19. The process of claim 5, wherein removing the polar solvent is done by flash evaporation.

20. The process of claim 9, wherein said fermentation grade glycerol is salt-containing glycerol.

21. The process of claim 20, further comprising the step of tailoring said salt content of said fermentation grade glycerol to between about 0.05 to about 8.2 percent salt.

22. The process of claim 20, further comprising the step of tailoring said salt content of said fermentation grade glycerol to between about 0.05 to about 3.5 percent salt.

23. The process of claim 20, further comprising the step of tailoring said salt content of said fermentation grade glycerol to between about 0.05 to about 1.0 percent salt.

24. The process of claim 2 wherein the separation occurs by at least one of gravity decantation, hydrocyclone separation, and centrifugal separation.

25. The process of claim 2 further comprising the step of heating the mixture of crude glycerol and hydrophobic solvent to between about 20° C. to about 95° C.

26. The process of claim 2 further comprising the step of heating the mixture of crude glycerol and hydrophobic solvent to between about 55° C. to about 65° C.

27. The process of claim 2 further comprising the step of mixing the mixture of crude glycerol and hydrophobic solvent for between about 5 minutes to about 30 minutes.

28. The process of claim 3 wherein the drying occurs at between about 60° C. to about 130° C.

* * * * *